United States Patent
Carreras et al.

(10) Patent No.: US 6,875,576 B2
(45) Date of Patent: Apr. 5, 2005

(54) METHOD FOR EVALUATING THERAPEUTIC EFFICACY

(75) Inventors: Christopher Carreras, Belmont, CA (US); Susan Dillon, Wayne, PA (US)

(73) Assignee: Kosan Biosciences, Inc., Hayward, CA (US)

(*) Notice: Subject to any disclaimer, the term of this patent is extended or adjusted under 35 U.S.C. 154(b) by 178 days.

(21) Appl. No.: 10/077,461

(22) Filed: Feb. 15, 2002

(65) Prior Publication Data

US 2002/0192709 A1 Dec. 19, 2002

Related U.S. Application Data

(60) Provisional application No. 60/269,631, filed on Feb. 15, 2001.

(51) Int. Cl.[7] ............................................. G01N 33/567
(52) U.S. Cl. ........................ 435/7.1; 435/7.2; 435/7.21; 436/501
(58) Field of Search ...................... 435/7.1–21; 436/501

(56) References Cited

U.S. PATENT DOCUMENTS

| | | | |
|---|---|---|---|
| 4,677,097 A | 6/1987 | Omura et al. | 514/29 |
| 5,854,407 A | 12/1998 | Harada et al. | 536/7.2 |

FOREIGN PATENT DOCUMENTS

| | | |
|---|---|---|
| WO | WO 93/13780 | 7/1993 |

OTHER PUBLICATIONS

Feighner et al. Receptor for Motilin Identified in the Human Gastrointestinal System, SCIENCE 284:2184–2188, Jun. 25, 1999.*

Riccobene et al. Modeling Activation and Desentization of G–protein Coupled Receptors Provides Insight into Ligand Efficacy. J. Theor. Biol. 200:207–222, 1999.*

* cited by examiner

*Primary Examiner*—John Ulm
(74) *Attorney, Agent, or Firm*—Morrison & Foerster LLP

(57) ABSTRACT

The present invention relates to in vitro methods for evaluating compounds that better correlate with therapeutic efficiency than evaluating compounds based on potency alone. In general, the inventive method comprises: (i) determining a potency value for a compound against its target receptor; (ii) determining a desensitization value for the compound against its target receptor; and (iii) comparing the potency value with the desensitization value. If the desired action of a compound is as a receptor agonist, then the compound's desensitization value should be larger than the compound's potency value. This ensures that the concentration of a compound required for potency will not also cause the receptor to desensitize at the same time, thus in an essence nullifying the desired effect. The inventive methods are used to evaluate novel motilide compounds as well as ABT-229 and EM-574, two motilide compounds for which clinical trials have been initiated.

8 Claims, 5 Drawing Sheets

METHOD FOR EVALUATING THERAPEUTIC EFFICACY

CROSS-REFERENCE TO RELATED APPLICATIONS

This application claims priority to U.S. provisional patent application Ser. No. 60/269,631, filed 15 Feb. 2001, entitled METHOD FOR EVALUATING THERAPEUTIC EFFICACY, by inventors Chris Carreras and Sue Dillon, which is incorporated herein in its entirety.

STATEMENT OF GOVERNMENT INTEREST

This invention was supported in part by NIH Grant No. DK57380. The United States government has certain rights in this invention.

BACKGROUND

Many potential drug candidates are withdrawn from further development because their promising in vitro results do not translate into therapeutic efficacy during clinical trials. Because the time and cost of taking a compound into clinical trials can be as much as ten years and 200 million dollars, failure of a potential drug at the clinical phase is enormous.

For potential drug candidates that act as receptor agonists, receptor desensitization may contribute to the disconnect between in vitro potency and lack of clinical efficacy. Receptor desensitization typically occurs upon continued stimulation of the receptors with agonists. When receptors are initially exposed to an agonist, the initial response usually peaks and then decreases to some tonic level. If the agonist is removed for a brief period, this state of receptor desensitization is maintained such that a second addition of the agonist provokes a diminished response. Removal of the agonist for a more extended period of time generally allows the receptors to reset its capacity for maximal response.

There are two types of desensitization: homologous and heterologous desensitization. Homologous desensitization is defined as the reduced response of a receptor induced only by the agonist that has stimulated the receptor. Heterologous desensitization is defined as the reduced response of a receptor induced by something other than the agonist for that receptor. For example, receptors for different hormones that act on a single signaling pathway may become less effective when only one of the receptors is continuously stimulated. Such heterologous desensitization may result either from modification of each receptor by a common feedback mechanism or from effects exerted at some common point in the effector pathway distal to the receptor itself.

Despite the importance of receptor desensitization, drug discovery efforts generally focus on agonist potency. However, because receptor desensitization can have a profound effect on clinical efficacy, methods for evaluating and incorporating receptor desensitization for therapeutic uses are needed and desired.

SUMMARY

The present invention relates to in vitro methods for evaluating compounds that better correlate with therapeutic efficiency than evaluating compounds based on potency alone. In general, the inventive method comprises: (i) determining a potency value for a compound against its target receptor; (ii) determining a desensitization value for the compound against its target receptor, and (iii) comparing the potency value with the desensitization value. If the desired action of a compound is as a receptor agonist, then the compound's desensitization value should be larger than the compound's potency value. This ensures that the concentration of a compound required for potency will not also cause the receptor to desensitize at the same time, thus in an essence nullifying the desired effect.

DETAILED DESCRIPTION OF THE DRAWINGS

Figure 1:
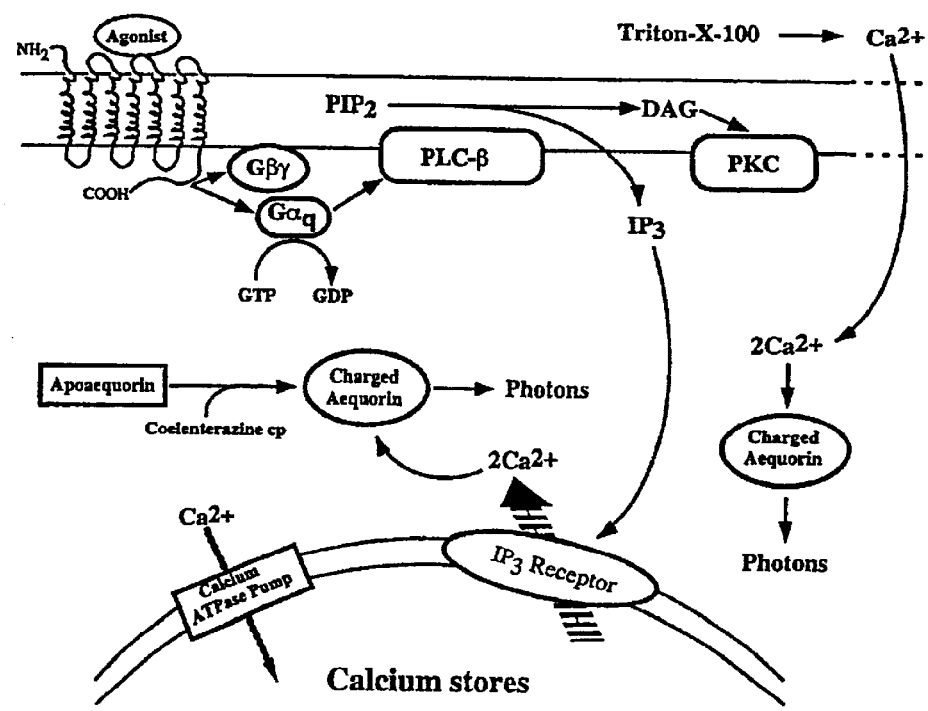
FIG. 1 is a schematic illustrating the principle of measuring GPCR agonism via aequorin.

FIG. 1 is a schematic illustrating the principle of measuring GPCR agonism via aequorin. Briefly, agonist binding to a GPCR causes dissociation of the $G_\alpha$ subunit from the $G_{\beta\gamma}$ subunits and hydrolysis of GTP to $GDP+P_i$. $G_\alpha$ then activates $PLC_\beta$, which generates $IP_3$. The $IP_3$ targets a receptor that causes $Ca^{++}$ release from intracellular stores. $Ca^{++}$ binding by aequorin causes oxidation of the coelenterazine cofactor with accompanying photon release. Following agonist stimulation, triton X-100 lysis of the cell exposes the remaining aequorin to $Ca^{++}$. A value F is calculated by dividing the agonist response by the sum of the agonist and triton X-100 responses.

Figure 2:
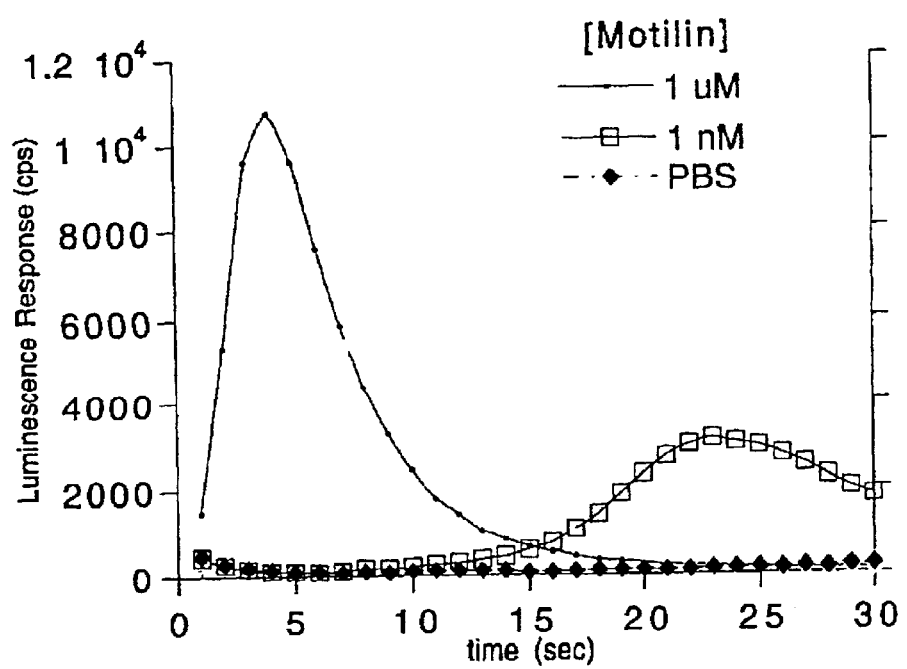
FIG. 2 is a graph depicting the luminescence response of 50,000 HEK293 cells stably expressing aequorin and the motilin receptor.

FIG. 2 is a graph depicting the luminescence response of 50,000 HEK293 cells stably expressing aequorin and the motilin receptor upon exposure to the indicated concentration of motilin. The y-axis reflects the luminescence response in cps and the x-axis reflects the time in seconds. Concentrations of motilin and provided.

Figure 3:
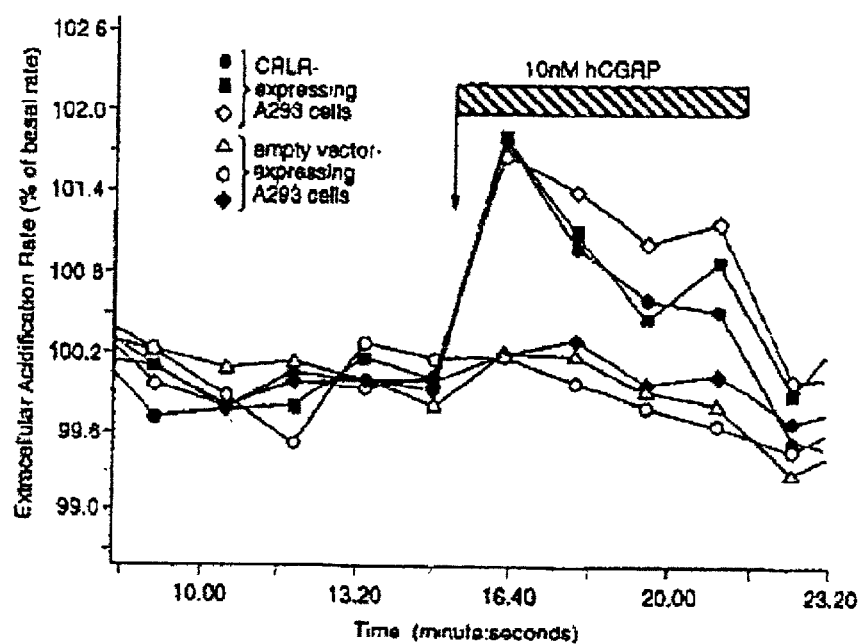
FIG. 3 is a graph depicting the orphan receptor CRLR (calcitonin receptor-like receptor) expressed transiently in HEK 293 cells.

FIG. 3 is a graph depicting the orphan receptor CRLR (calcitonin receptor-like receptor) expressed transiently in HEK 293 cells. This expression mediates a specific extracellular acidification response when challenged with 10 nM human CGRP. Each point represents the acidification response from an individual chamber of cells.

Figure 4:
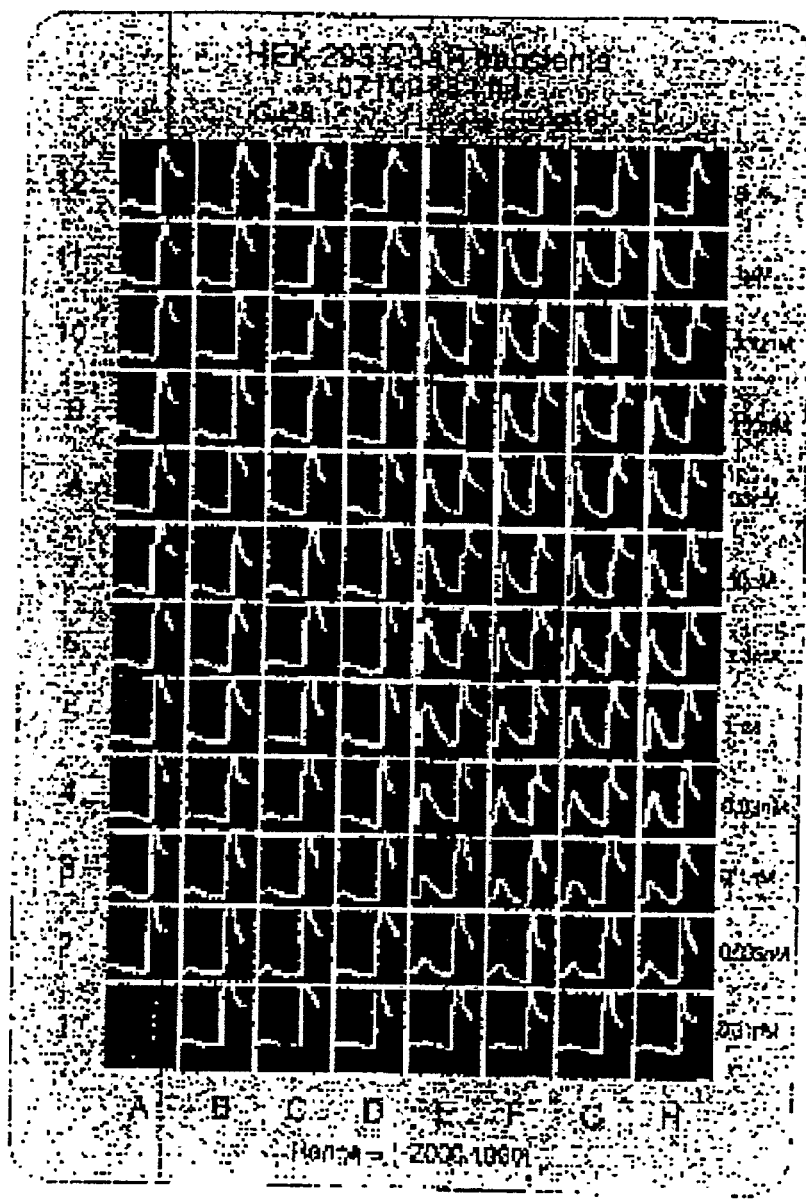
FIG. 4 is a schematic representation of the $Ca^{2+}$ mobilization responses of the C3a receptor.

FIG. 4 depicts $Ca^{2+}$ mobilization responses of the C3a receptor expressed with and without the promiscuous G protein $G\alpha_{16}$. Each square represents responses as determined simultaneously via FLIPR from an individual microtiter plate well of cells. The y axis in each square corresponds to intracellular calcium levels and the x axis corresponds to time. The left-hand response of each trace corresponds to challenge with C3a (or buffer) as indicated; the right-hand response of each trace corresponds to challenge with 200 μM muscarine as an internal control for each well. Columns A–D were generated using HEK 293 cells transfected with C3a receptor and columns E–H were generated using cells transfected with both C3a receptor and $G\alpha_{15}$. Quantitation of these data is presented in FIG. 5.

Figure 5:
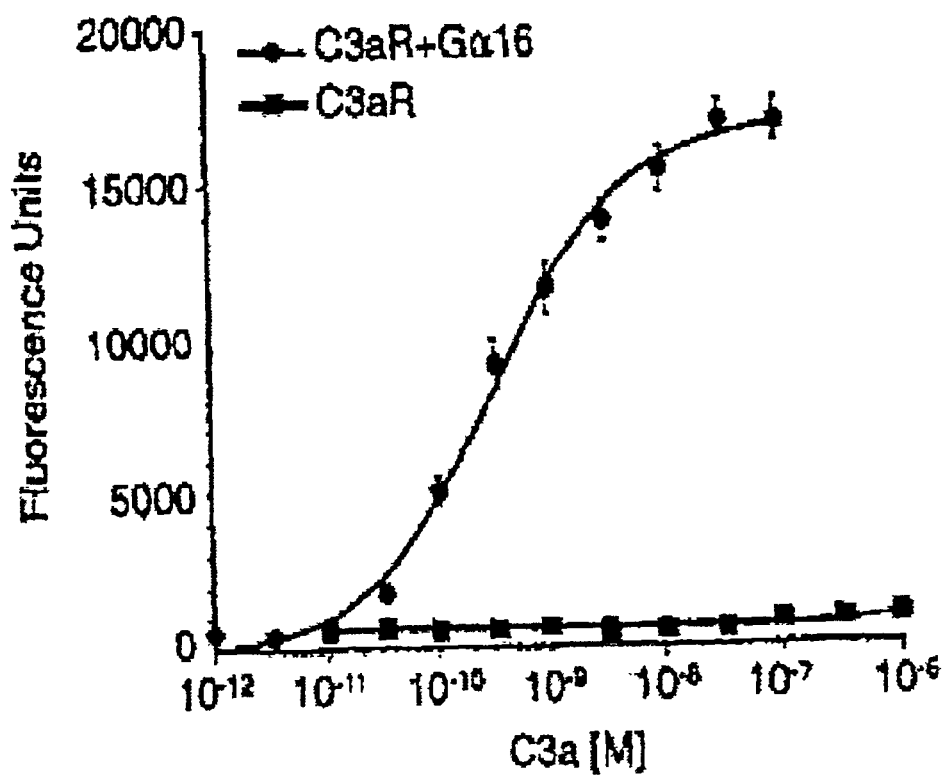
FIG. 5 is a graph depicting calcium mobilization induced by C3a in HEK 293 cells transiently transfected with the C3a receptor.

FIG. 5 shows calcium mobilization induced by C3a in HEK 293 cells transiently transfected with C3a receptor, alone (■) or C3a receptor with $C\alpha_{16}$ (●). The maximum $Ca^{2+}$ response (peak height) following C3a addition to each well, as illustrated in FIG. 4 was used to construct the
} dose-response curves. Each point in FIG. 5 represents the mean 4 SEM of eight determinations.

DESCRIPTION OF THE PREFERRED EMBODIMENTS

The present invention relates to methods for evaluating the therapeutic efficacy of potential drugs that act as receptor agonists. In a typical drug discovery effort, these compounds are primarily evaluated on their ability to elicit a response upon binding to their respective target receptors. The ability to elicit a response is also referred to as a compound's potency and is most often expressed in terms of an $EC_{50}$ value, or the concentration of a compound that elicits 50% of a maximal response. Potency generally remains the primary consideration throughout the initial in vitro screening assays and sometimes throughout the preclinical evaluation assays.

However, the focus on potency can result in potential drug candidates that fail during clinical trials for lack of therapeutic efficacy. In addition to potency, desensitization should also be considered because the binding of agonists over time to their respective receptors can effectuate an increasingly diminished response. This phenomenon is an inherent part of receptor's mechanism of action. Desensitization is expressed in terms of a concentration that inhibits the original receptor response and is most often expressed in terms of an $IC_{50}$ value, or the concentration of a compound that inhibits 50% of a maximal response.

Despite the recognition that potency and desensitization are part of a receptor's mechanism of action, a method that considers both potency and desensitization when evaluating a potential drug candidate is not in the prior art. The present invention provides such a method.

In general, the inventive method comprises: (i) determining a potency value for a compound against its target receptor; (ii) determining a desensitization value for the compound against its target receptor; and (iii) comparing the potency value with the desensitization value. If the desired action of a compound is as a receptor agonist, then the compound's desensitization value should be larger than the compound's potency value. This ensures that the concentration of a compound required for potency will not also cause the receptor to desensitize at the same time, thus in an essence nullifying its effect. In preferred embodiments, the potency value and the desensitization value are calculated using similar reaction conditions. For example, if a cell-free receptor assay is used to calculate the potency value, then the same system should also be used to calculate the desensitization value. Similarly, the potency value and the desensitization value should be expressed in a like manner. For example, if the potency value is expressed in terms of $EC_{50}$, then the desensitization value should be expressed in terms of $IC_{50}$; if the potency value is expressed in terms of $EC_{90}$, then the desensitization value should be expressed in terms of $IC_{90}$.

In one aspect of the present invention, the comparison of the potency value and the desensitization value is accomplished by calculating a ratio of the desensitization value to the potency value. This ratio is termed the "efficacy index". A ratio of approximately equal to one indicates that the concentration required for potency is similar to the concentration required for desensitization. In other words, because the concentration required for the desired biological response is also the concentration that induces desensitization, the compound is not likely to be therapeutically effective if the desired response is receptor activation. Under these circumstances, the concentration required for the desired biological response should be well below the concentration that induces desensitization. In preferred embodiments, the efficacy index is at least 10 and more preferably at least 25. In even more preferred embodiments, the efficacy index is at least 50. An efficacy index greater than about 100 is most preferred. However, if the desired response were desensitization, the compounds whose desensitization value is about equal to the potency value or less than the potency value would be preferred.

In another aspect of the present invention, a screening method for GPCRs is provided. For GPCRs that causes a calcium ion ("$Ca^{++}$") influx upon activation (GPCRs that signal through the phosphatidyl inositol and calcium pathways such as motilin receptor and serotonin receptors (e.g., 5HT2a and 5HT2c)), the method comprises expressing a gene encoding a GPCR and expressing a gene for aequorin in a cell line. For GPCRs that do not cause a calcium ion influx upon activation in the native state, the method comprises expressing a gene encoding the GPCR with a promiscuous $G_\alpha$ such as $G_{\alpha 16}$ and a gene for aequorin in a cell line. The coexpression of a GPCR with a promiscuous $G_\alpha$ is described in, for example, Stables et al, Analytical Biochemistry 252: 115–126 (1997) which is incorporated herein by reference.

Methods for measuring the potency value comprise exposing the cell line (expressing a GPCR and aequorin) to a test compound and measuring the resulting luminescence. Methods for measuring the desensitization value comprise pretreating the cell line to a test compound, exposing the cell line to a known agonist, and measuring the resulting luminescence. When the resulting cells are exposed to the agonists of the cloned receptor, the activated receptor causes a calcium ion influx that, in turn, causes the aequorin to emit a flash of light. The amount of light emitted is proportional to the both the number of cells used and the degree of receptor response. Methods for measuring the potency value and the desensitization value comprise exposing cells expressing a GPCR and aequorin to a test compound and measuring the resulting luminescence. Methods for measuring the desensitization value comprising exposing cells expressing a GPCR and aequorin to a test compound; removing the test compound from the cells; exposing the cells to a GPCR agonists; and measuring the resulting luminescence. Protocols for expression and receptor assays are further described in Examples 1 and 2. The potency and desensitization values are then compared and evaluated for each test compound as previously described.

Illustrative Application of the Inventive Methods

The methods of the present invention is further illustrated with specific reference to the motilin receptor. Motilin is a 22 amino acid peptide that, upon binding to the motilin receptor stimulates gastric motility. Non-peptide agonists of the motilin receptor are being evaluated as prokinetic agents for the treatment of disorders where enhanced gastrointestinal motility is indicated or desired. Illustrative examples of such disorders include but are not limited to gastroparesis, gastroesophageal reflux disease, anorexia, gall bladder stasis, postoperative paralytic ileus, scleroderma, intestinal pseudoobstruction, gastritis, emesis, and chronic constipation (colonic inertia).

A promising new class of prokinetic agents, motilides are macrolide compounds such as erythromycin and its derivatives that are agonists of the motilin receptor. Certain motilides have been shown to induce muscular contractions in the stomach and small intestines, increase esophageal peristalsis, and acceleration of gastric emptying in patients with gastric paresis. In fact, clinical trials have been initiated for several motilides including ABT-229 (1) and EM-574 (2) whose structures are shown below.

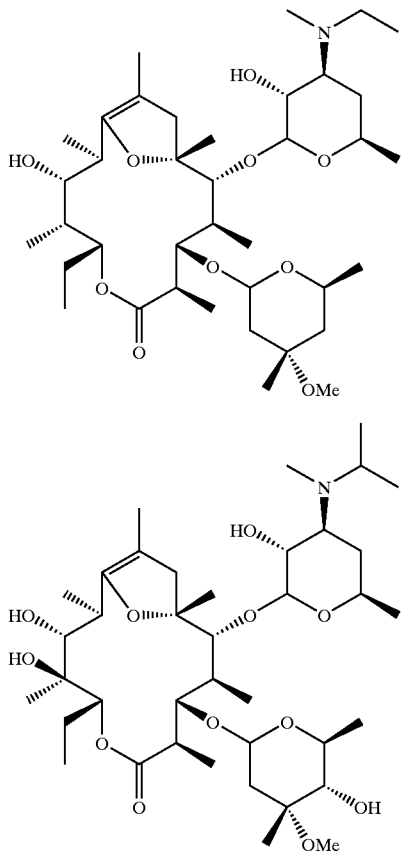

However, based upon the inventive methods, neither ABT-229 nor EM-574 would have been predicted to be good drug candidates.

The motilin receptor and aequorin were co-expressed and an efficacy index was calculated for erythromycin 6,9-enol ether 3, ABT-229 and EM-574.

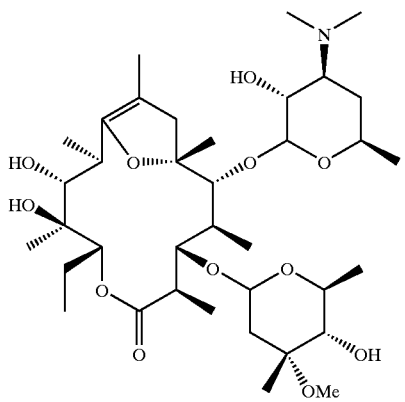

The efficacy index for erythromycin 6,9-enol ether is greater than 20,000 and the efficacy index for both ABT-229 and EM-574 are each less than 10. Although erythromycin 6,9-enol ether possess the potency ($EC_{50}$ in the nanomolar range) and the efficacy index to be a good drug candidate, the compound is unstable in acid and degrades in the stomach environment to a non-functional degradation product. ABT-229 has recently been pulled from clinical trials for lack of efficacy in treating gastroesophageal reflux disease. See Van Her Waarde et al., Aliment Pharmacol Ther 14: 453–462 (2000). Based on the efficacy index, EM-574 is predicted to suffer the same fate. The lesson of compounds like ABT-229 and EM-574 is that desensitization plays a role in determining therapeutic efficacy and that it should be considered early on in the evaluation process.

Applying the lessons of ABT-229 and EM-574, novel compounds are evaluated according to the methods of the present invention. The compounds are of the formula:

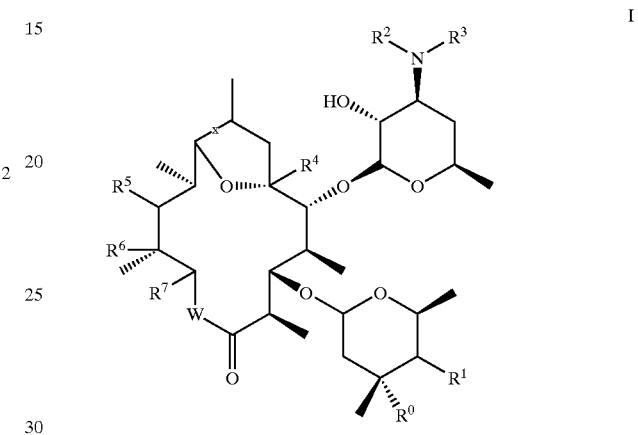

wherein:

W is O or NR;

R is hydrogen, $C_1$–$C_{10}$ alkyl, $C_2$–$C_{10}$ alkenyl, $C_2$–$C_{10}$ alkynyl, aryl, alkylaryl, alkenylaryl, or alkynylaryl;

$R^0$ is hydroxyl or methoxy;

$R^1$ is selected from the group consisting of hydrogen, hydroxyl, halide, $NH_2$, $OR^9$,

where $R^9$ is $C_1$–$C_{10}$ alkyl, $C_2$–$C_{10}$ alkenyl, $C_2$–$C_{10}$ alkynyl, aryl or heteroaryl and $R^{10}$ and $R^{11}$ are each independently hydrogen, $C_1$–$C_{10}$ alkyl, $C_2$–$C_{10}$ alkenyl, $C_2$–$C_{10}$ alkynyl, or aryl;

$R^2$ and $R^3$ are each independently selected from the group consisting of hydrogen, $C_1$–$C_{10}$ alkyl, $C_2$–$C_{10}$ alkenyl, $C_2$–$C_{10}$ alkynyl, aryl, alkylaryl, alkenylaryl, alkynylaryl or $R^2$ and $R^3$ together form a cycloalkyl or a cycloaryl moiety;

$R^4$ is hydrogen or methyl;

$R^5$ is hydrogen, hydroxyl or oxo;

$R^6$ is hydroxyl, $OR^{12}$ where $R^{12}$ is $C_1$–$C_{10}$ alkenyl, or $C_2$–$C_{10}$ alkynyl;

$R^7$ is methyl, $C_3$–$C_{10}$ alkyl, $C_2$–$C_{10}$ alkenyl, $C_2$–$C_{10}$ alkynyl, alkylaryl, alkenylaryl, alkynylaryl, amidoalkylaryl, amidoalkenylaryl, or amidoalkynylaryl; and, x is a single or a double bond. Compounds of formula I wherein the desensitization value is greater than the potency value are good drug candidates. In preferred embodiments, the desensitization value is at least 10 times the potency value. In more preferred embodiments, the desensitization value is at least 25 times the potency value. In even more preferred embodiments, the desensitization value is at least 50 times the potency value. Compounds of formula I wherein the desensitization value is at least 100 times the potency value are most preferred.

Many of the compounds contain one or more chiral centers. All of the stereoisomers are included within the scope of the invention, as pure compounds as well as mixtures of stereoisomers. Similarly, all geometric isomers are also included within the scope of the invention.

As used herein, the term "alky" refers to an optionally substituted straight, branched or cyclic hydrocarbons. "Alkenyl" refers to an optionally substituted straight, branched, or cyclic chain hydrocarbon with at least one carbon—carbon double bond. "Alkynyl" refers to an optionally substituted straight, branched, or cyclic hydrocarbon with at least one carbon—carbon triple bound. Substituted alkyl, substituted alkenyl, or substituted alkynyl refer to the respective alkyl, alkenyl or alkynyl group substituted by one or more substituents. Illustrative examples of substituents include but are not limited to alkyl, alkenyl, alkynyl, aryl, halo; trifluoromethyl; trifluoromethoxy; hydroxy; alkoxy, cycloalkoxy; heterocyclooxy; oxo (=O); alkanoyl (—C(=O)-alkyl); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., SO$_2$NH$_2$); substituted sulfonamido; nitro; cyano; carboxy; carbamyl (e.g., CONH$_2$); substituted carbamyl (e.g., —C(=O)NR'R" where R' and R" are each independently hydrogen, alkyl, aryl, aralkyl and the like); alkoxycarbonyl, aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with halogen, alkyl, alkoxy, aryl, or aralkyl and the like.

The term "aryl" refers to an optionally substituted aromatic ring having 6 to 12 carbon atoms and may include one or more heteroatoms such as N, S and O. Illustrative examples of aryl include but are not limited to biphenyl, furyl, imidazolyl, indolyl, isoquinolyl, naphthyl, oxazolyl, phenyl, pyridyl, pyrryl, quinolyl, quinoxalyl, tetrazoyl, thiazoyl, thienyl and the like. Substituted aryl refers to an aryl group substituted by, for example, one to four substituents such as substituted and unsubstituted alkyl, alkenyl, alkynyl, and aryl; halo; trifluoromethoxy; trifluoromethyl; hydroxy; alkoxy; cycloalkyloxy; heterocyclooxy; alkanoyl; alkanoyloxy; amino; alkylamino; aralkylamino; cycloalkylamino; heterocycloamino; dialkylamino; alkanoylamino; thio; alkylthio; cycloalkylthio; heterocyclothio; ureido; nitro; cyano; carboxy; carboxyalkyl; carbamyl; alkoxycarbonyl; alkylthiono; arylthiono; alkylsulfonyl; sulfonamido; aryloxy; and the like. The substituent may be further substituted, for example, by halo, hydroxy; alkyl, alkoxy; aryl, substituted aryl, substituted alkyl, substituted aralkyl, and the like.

The terms "alkylaryl" or "arylalkyl" refer to an aryl group bonded directly through an alkyl group, such as benzyl. Similarly, "alkenylaryl" and "arylalkenyl" refer to an aryl group bonded directly through an alkenyl group and "alkynylaryl" and "arylalkynyl" refer to an aryl group bonded directly through an alkynyl group.

The term amidoalkylaryl refer to a group of the formula —ZNH—(C=O)—R'R" where Z may be present or absent, and Z and R're each independently an optionally substituted C$_1$–C$_{10}$ alkyl, alkenyl, or alkynyl and R' is an optionally substituted aryl.

The terms "halogen," "halo", or "halide" refer to fluorine, chlorine, bromine and iodine.

The term "erythromycin" refers to a compound of the formula

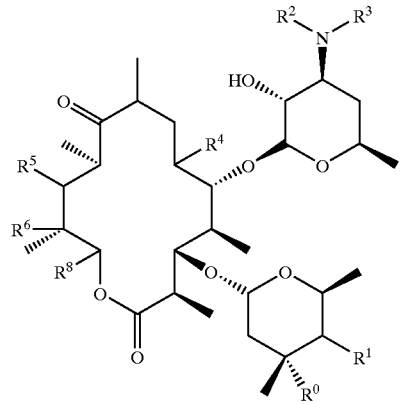

and derivatives and analogs thereof where R$^8$ is ethyl or R$^7$ and R$^0$, R$^1$, R$^2$, R$^3$, R$^4$, R$^5$, R$^6$ and R$^7$ are as described herein.

Free hydroxyl groups in the compounds of the present invention may optionally be protected with a hydroxyl protecting group. The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2$^{nd}$ edition, John Wiley & Sons, New York (1991), which is incorporated herein by reference. Illustrative hydroxyl protecting groups include but not limited to tetrahydropyranyl; benzyl; methylthiomethyl; ethythiomethyl; pivaloyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl and the like; acyl and aroyl such as acetyl, pivaloylbenzoyl, 4-methoxybenzoyl, 4-nitrobenzoyl and aliphatic acylaryl and the like. Hydroxyl protected versions of the inventive compounds are also encompassed within the scope of the present invention.

In addition to the explicit substitutions at the above-described groups, the inventive compounds may include other substitutions where applicable. For example, the erythromycin backbone or backbone substituents may be additionally substituted (e.g., by replacing one of the hydrogens or by derivatizing a non-hydrogen group) with one or more substituents such as C$_1$–C$_5$ alkyl, C$_1$–C$_5$ alkoxy, phenyl, or a functional group. Illustrative examples of suitable functional groups include but are not limited to alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, hydrazide, enamine, sulfone, sulfide, sulfenyl, and halogen.

In another embodiment of the present invention, the compounds are of the formula I wherein: W is O or NR; R is hydrogen, C$_1$–C$_5$ alkyl, aryl, or alkylaryl; R$^0$ is hydroxyl or methoxy; R$^1$ is hydrogen or hydroxyl; R$^2$ and R$^3$ are each independently $C_1$–$C_5$ alkyl, phenyl or benzyl; $R^4$ is methyl; $R^5$ is hydroxyl or oxo; $R^6$ is hydroxyl or $C_1$–$C_5$ alkoxy, $R^7$ is methyl, $C_3$–$C_5$ alkyl, $C_2$–$C_5$ alkenyl, $C_2C_5$ alkynyl, aryl, alkylaryl or alkenylaryl; and, x is single bond or a double bond.

In another embodiment, the compounds are of the formula I wherein: W is O or NR; R is hydrogen, methyl, ethyl, propyl, isopropyl, phenyl or benzyl; $R^0$ is hydroxyl or methoxy; $R^1$ is hydrogen or hydroxyl; $R^2$ is methyl; $R^3$ is methyl, ethyl, propyl, isopropyl, butyl, isobutyl, secbutyl or tertbutyl; $R^4$ is methyl; $R^5$ is hydroxyl; $R^6$ is hydroxyl or methoxy; $R^7$ is methyl, vinyl, propyl, isobutyl, pentyl, prop-2-enyl, propargyl, but-3-enyl, 2-azidoethyl, 2-fluoroethyl, 2-chloroethyl, cyclohexyl, phenyl, or benzyl; and, x is a single or a double bond.

In another embodiment, the compounds are of the formula I wherein: W is O or NH; $R^0$ is methoxy; $R^1$ is hydrogen or hydroxyl; $R^2$ is methyl; $R^3$ is methyl, ethyl, or isopropyl; $R^4$ is methyl; $R^5$ is hydroxyl; $R^6$ is hydroxyl or methoxy; $R^7$ is propyl, but-3-enyl, 2-azidoethyl, phenyl, or benzyl; and, x is a single or a double bond.

In another embodiment, the present invention provides compounds of the following formulas

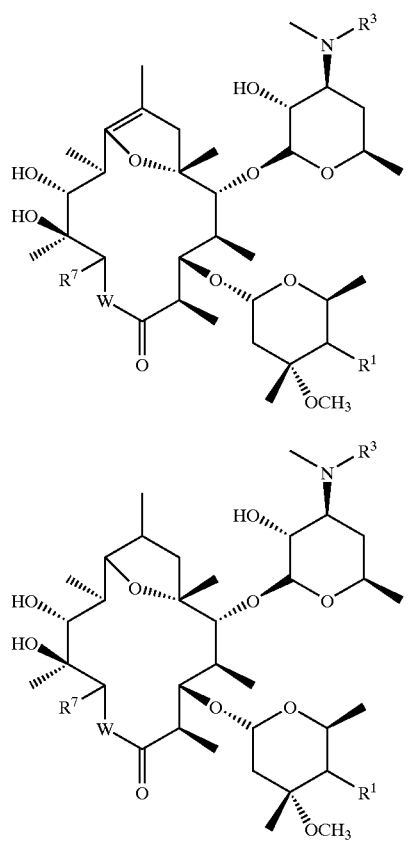

wherein: W is O or NH; $R^1$ is hydrogen or hydroxyl; $R^3$ is methyl, ethyl, or isopropyl; and $R^7$ is propyl.

In one aspect of the present invention, compounds of formulas I, II, or III possessing an efficacy index of greater than about 10 are provided. In another aspect of the present invention, compounds of formulas I, II, or III possessing an efficacy index of greater than about 100 are provided. In yet another aspect of the present invention, compound of formulas I, II, or III possessing an efficacy index of greater than about 1000 are provided. Because both potency and desensitization are considered, these compounds are believed to possess therapeutic efficacy for their intended purposes.

As used herein, the term "agonist" can refer to any compound that stimulates activity at a receptor or receptors normally stimulated by naturally occurring substances, thus triggering a response.

As used herein, the term "GPCR" refers to a G protein coupled receptor.

A test compound can be, for example, a small molecule, a nucleic acid, a protein, a carbohydrate, a lipid, or any combination or portion thereof. In addition, the test compound can be in singular form or in a library.

The use of aequorin as an indicator in cells expressing a GPCR is merely exemplary. Any indicators know to one skilled in the art, such as fluorescent proteins, radiolabels, or antibodies, for example, can be used in the method of the present invention. For example, fluorescent calcium indicator dyes such as Fluo-3 and Fluo-4 can be used to reflect changes in intracellular calcium levels. In addition, changes in pH can be measured by a Cytosensor, as described below, indicating changes in extracellular acidification rates. It should be understood based on the disclosure provided that the invention is not limited to a motilin receptor based assay using aequorin as an indicator.

Starting Materials

The compounds of the present invention can be prepared in accordance with the methods of the present invention by a combination of recombinant DNA technology and organic chemistry.

In regards to recombinant DNA technology, the practice of the present invention will employ, unless otherwise indicated, conventional techniques of cell biology, cell culture, molecular biology, and microbiology, which are within the skill of one skilled in the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); DNA Cloning, Volumes I and II (D. N. Glover ed., 1985); *Oligonucleotide Synthesis* (M. J. Gait ed., 1984); Mullis et al. U.S. Pat. No. 4,683,195: *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney. Alan R. Liss, Inc., 1987); *Immobilized Cell And Enzymes* (IRL, Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); and *Methods In Enzymology,* Vols. 154 and 155 (Wu et al. eds.).

Recombinant techniques are used to provide, in many instances, "unnatural" erythromycins or erythromycin derivatives that differ in one or more positions from the naturally occurring erythromycins A, B, C, or D. Although any suitable recombinant means may be used, a useful starting point is the complete 6-dEB synthase gene cluster that has been cloned in vectors and thus is amenable to genetic manipulations in *E. coli* and expression of the polyketide in *Streptomyces*. See U.S. Pat. Nos. 5,672,491; 5,830,750; 5,843,718; 5,712,146; and 5,962,290 which are all incorporated herein by reference. Once the aglycone is formed, it is next hydroxylated and/or glycoslyated and/or methylated at the appropriate positions by a converter strain that possesses the desired functionalities.

A particularly useful converter strain is an *Saccharopolyspora erythraea* eryA mutant that is unable to produce 6-dEB but can still carry out the desired conversions (Weber et al., J. Bacteriol. 164(1): 425–433 (1985). This mutant strain is able to take exogenously supplied 6-dEB and process it to erythromycin A by converting it into erythronolide B, 3-α-mycarosylerythronolide B, erythromycin D, erythromycin C, and finally to erythromycin A. An alternative route to erythromycin A is through erythromycin B where exogenously supplied 6-dEB is converted into erythronolide B, 3-α-mycarosylerythronolide B, erythromycin D, erythromycin B, and finally to erythromycin A. Other mutant strain, such as eryB, eryC, eryG, and/or eryK mutants, or mutant strains having mutations in multiple genes can be used to make compounds having any combinations of hydroxylations at C-6 and C-12, glycosylations at C-3 and C-5, and methylation at C-3"-OH. Any of these products may be used as starting materials for the practice of the present invention.

Erythromycins where the substituent at C-13 is methyl or ethyl, the 6-deoxyerythronolide B synthase ("DEBS") from *S. erythraea* can be used in a recombinant expression system described in U.S. Pat. No. 5,672,491 to produce the aglycone in *Streptomyces coelicolor*. Optionally, the oleandolide or megalomicin polyketide synthase ("PKS") genes may be used in this expression system. See PCT publications WO 01/27284 and WO 00/26349, each of which is incorporated herein by reference.

For erythromycins where the substituent at C-13 is something other than methyl or ethyl, one can employ a technique known as chemobiosynthesis in which activated thioesters called SNAC-diketides are converted to 13-substituted 6-dEB derivatives (13-R-13-desethyl-6-dEB compounds) by fermentation of *S. coelicolor* CH999/pJRJ2 or functionally similar strains that contain a PKS in which the ketosynthase domain of module 1 has been inactivated by mutation (the KS1° mutation). This methodology is described in PCT Publication Nos. WO 97/02358 and WO 99/03986 and U.S. Pat. No. 6,066,721 which are all incorporated herein by reference. Additional SNAC-diketide compounds and the corresponding aglycones are described in PCT Publication No. WO 00/44717 which is incorporated herein by reference.

6-dEB and 6-dEB derivatives such as 13-substituted 6-dEB are converted into the desired erythromycin starting material by an appropriate converter strain. For example, any one of the post PKS products may be used as starting materials such as 13-substituted counterparts (where the ethyl group which normally exists at C-13 is replaced with another substituent) to: erythronolide B, 3-α-mycarosylerythronolide B, erythromycin D, erythromycin B, erythromycin C, and erythromycin A. In particular, 13-substituted erythromycin A can be made by fermentation with an eryA mutant that is incapable of producing 6-dEB but can still carry out the desired conversions. 13-substituted erythromycin B can be made by fermentation with an eryA mutant that is incapable of producing 6-dEB and in which the ery K (12-hydroxylase) gene has been deleted or otherwise rendered inactive. Alternatively, erythromycin B derivatives can be made in a KS1°/eryK mutant strain of *S. erythaea*. The general method for using chemobiosynthesis for making modified 6-dEB is illustrated by Example 6 with specific reference to 13-propyl-6-dEB (13-propyl-13-desethyl-6-dEB). The general method for converting modified 6-dEB compounds to the desired hydroxylated and glycosylated form by using an eryA converter strain is illustrated by Example 7 with specific reference to converting 13-propyl 6-dEB to 13-propyl erythromycin A (13-propyl-13-desethyl-erythromycin A).

Synthetic Methods

The methods described herein are generally applicable to all erythromycins and erythromycin derivatives (e.g., erythromycins A, B, C, and D, 13-substituted erythromycins A, B, C, and D, erythronolide B, 3-α-mycarosylerythronolide B, and derivatives thereof) unless explicitly limited. As such references to specific embodiments are for the purposes of illustration only and are not intended to limit in any way the scope of the present invention.

Enol ether compounds are also referred to as 6,9-enol ether erythromycins or 8,9-anhydro erythromycin 6,9-enol ethers, or dihydrofurans. The 6,9-epoxides are also referred to as epoxides or as tetrahydrofurans. Unless expressly limited these terms may refer to both the lactone (W=O) or lactam (W=NR) compounds.

Enol ether compounds where W=O are formed by treating an erythromycin starting material with mild acid. The corresponding epoxide is formed by reducing the carbon—carbon double bond between C-9 and C-9 of the enol ether. An alternate method for forming epoxide compounds (where W=O) is where the free hydroxyls of erythromycin are protected and the C-9 oxo is reduced to a sodium borohydride to a 9-dihydro-erythromycin intermediate (where C-(is —CHOH—). Illustrative examples of suitable protecting groups include acetyl for the C-2' and C-4" hydroxyls and a cyclic carbamate for the C-11 and C-12 hydroxyls. The hydroxyl group at C-9 is subsequently activated and displaced to form the desired epoxide product.

The enol ether and epoxide compounds (where W=O) may optionally be converted into the corresponding lactams (where W=NR). The enol ether or epoxide lactone is treated with potassium carbonate to from a 12-membered derivative which is treated with Martin sulfurane to form the 12-membered 12,13 epoxide. This 12,13 epoxide is reacted with NH$_2$R to form the erythromycin lactam.

Derivatives of the enol ether and epoxide lactones and lactams may be made by making the desired modifications. For example 11-oxo compounds are made by oxidizing the C-11 hydroxyl with carbodiimide and methylsulfoxide. C-12 alkoxy compounds are made by alkylating the C-12 hydroxyl group. Illustrative examples of other modifications include the demethylation and subsequent alkylation of the 3'N and the modifications at the C-3" hydroxyl group. Detailed protocols of these types of modifications are provided in the Examples.

Functional Assays for Screening Orphan Receptors

The methods of the present invention can be used in screening orphan receptors. In this instance, the choice of functional assays used for screening orphan receptors is crucial to success. The assays should be as generic as possible in order to pick up a wide range of coupling mechanisms. Measurements of metabolic activation of cells using the Cytosensor microphysiometer is probably the most generic assay available, but is hampered by its low throughput. Alternative assay systems in mammalian cells focus largely on measuring changes in intracellular cAMP or Ca$^{2+}$ levels, either directly using standard methods or via the use of reporter gene assays. It is becoming increasingly important to use high throughput assay systems to allow screening of relatively large libraries of compounds and peptides in microtiter plate format; 96-well or 384-well format assays can readily be developed for measurement of cAMP levels.

For fluorescence-based assays such as Ca$^{2+}$ mobilization, 96-well fluorescent plate readers offer greater throughput over conventional fluorimeters, but, standard plate-readers only allow sequential read-out from individual wells, which limits the rate of data capture when measuring rapid responses such as Ca$^{2+}$ mobilization. The use of a chargecoupled device (CCD) imaging camera to allow simultaneous 96-well fluorescent readout in real time—the FLIPR system developed by Molecular Devices—can dramatically increase throughput. Since the coupling pathway for a particular receptor is difficult to predict de novo from sequence information, a variety of assay systems should be used when screening orphan receptors.

The Cytosensor Microphysiometer

The principles of microphysiometry as employed by the Cytosensor microphysiometer (Molecular Devices) have been fully described elsewhere, but essentially the approach utilizes the detection of changes in extracellular acidification rates as a generic measurement of cellular metabolic activation when receptors on the cell surface are stimulated.

Briefly, cells are immobilized in close proximity to a light addressable potentiometric sensor (LAPS) which acts as a highly sensitive pH detector. A low buffer capacity "running medium" is perfused across the cells, and at regular time intervals the flow of the running medium is temporarily stopped. As a result, the medium surrounding the cells becomes progressively more acidic and this change in pH is detected by the LAPS. The rate of acidification during the slop-flow phase is the measured parameter. Typically, sampling of the extracellular acidification rate in this way occurs once every 1 to 2 min. depending upon the exact configuration of the assay. Most cell types can be maintained in the microphysiometer for several hours, allowing considerable time for data to be accumulated. Extracellular acidification rates are generally expressed as a percentage of basal rates immediately prior to the addition of test drug, and plotted against time (as in FIG. 3). An elegant fluidics system enables the operator to control the exposure of cells, to test drugs without flow artifacts.

As shown in FIG. 3, the orphan receptor CRLR (calcitonin receptor-like receptor) expressed transiently in HEK 293 cells, mediates a specific extracellular acidification response when challenged with 10 nM human CGRP. Each point represents the acidification response from an individual chamber of cells.

Use of Cytosensor Microphysiometer to Screen Orphan Receptors

The following protocol can be utilized to screen orphan receptors:

1. 48 h after receptor transfection, gently lift adherent cells from the flask by addition of 5 ml ethylene diamine tetraacetate (EDTA, 200 mg/l in phosphate-buffered saline without $Ca^{2+}$ and $Mg^{2+}$) for 1 to 2 min. Gently tap flask if necessary to detach cells. Aspirate the EDTA and add to 20 ml microphysiometer running medium (minimum essential medium, MEM, with Earle's salts without $NaHCO_3$, supplemented with 6.6 ml/l 4 M NaCl). Repeat the EDTA incubation until all the cells have detached.

2. Count cells, centrifuge for 5 min at 300×g, then resuspend in running medium to a concentration of 2 to 3×10$^6$ cells/100 μl.

3. Immobilize the suspension of transfected cells in agarose on a cell capsule cup assembly as follows: melt a 200 μl aliquot of agarose (cell entrapment kit, Molecular Devices, cat no. R8023) in boiling water and then bring to 37° C. in a heating block. Mix one volume of agarose with three volumes of cell suspension, in a prewarmed tube, by pipetting the mixture up and down several times, taking care not to introduce air bubbles, and not to allow the mixture to cool below 30° C. (below which it will solidify).

4. Transfer the cells into the microphysiometer by placing a blue spacer ring into the capsule cup, carefully spotting 10 μl of cell/agarose mixture into the center of the ring (taking care not to allow the mixture to touch the ring otherwise it will wick away from the center of the capsule), and allowing the mixture to solidify (2 to 3 min).

5. Carefully add 1 ml of running medium to the well holding the cup and 0.2 ml to the cup itself. Add an insert, and then 0.2 ml of running medium to the insert. When the insert has sunk to the bottom of the cup, the whole assembly may then be transferred to the cytosensor.

6. Set up the cytosensor microphysiometer as per manufacturer's instructions, with parameters set as follows: total pump cycle time=1 min, 30 s; 1 minute at 50% full speed, then 30 s pump off; "Get rate" from 1 min 8 s to 1 min 28 s. Chamber temperatures are set to 37° C. Allow at least 1 h for rates to stabilize before adding test ligands at 30 s into pump cycle.

The orphan G protein-coupled receptor CRLR (calcitonin receptor-like receptor) was identified as a calcitonin gene-related peptide (CGRP) receptor by Aiyar et al. following analysis of HEK 293 cells stably expressing the receptor in both functional (cAMP) and radioligand binding assays. However, other groups were unable to repeat this finding and there has been some speculation that CRLR is not the authentic CGRP receptor. The cytosensor microphysiometer is an alternative assay system that can be used to demonstrate that CRLR will produce a robust, specific response to CGRP when expressed transiently in HEK 293 cells (FIG. 3), confirming the findings of Aiyar et al. More recent publications are also consistent with this receptor functioning as a CGRP receptor when expressed under appropriate conditions.

$Ca^{2+}$ Mobilization

Changes in intracellular calcium levels can be routinely detected using fluorescent calcium indicator dyes such as Fluo-3 and Fluo-4. Cells are incubated with the acetoxymethyl ester form of the dye which permeates the cell membrane. Once inside the cell, the dye is converted to its free acid form by cleavage of the ester portion by intracellular esterases. This conversion renders the dye cell-impermeant, thus trapping it inside the cell. Only the free acid form and not the esterified counterpart will fluoresce on binding calcium ions and this property forms the basis of the assay.

Two methods are described for analyzing $Ca^{2+}$ mobilization responses; the first involves detection via a standard fluorescent plate reader (Fluoskan Ascent, Lab-Systems) and is suitable for cells in suspension; the second involves detection via FLIPR (Fluorometric Imaging Plate Reader: Molecular Devices), which has the ability to read all 96 wells of a microtiter plate simultaneously with data readouts every second, and is hence higher throughput. The FLIPR imagine system is configured in a semiconfocal manner, which renders it more suitable for use with adherent cells in monolayer. Sensitivity is also enhanced by eliminating background fluorescence from the fluid layer above the cells.

$Ca^{2+}$ Mobilization Measurements Using Fluoskan Ascent Fluorescent Plate Reader (Labsystems)

The following protocol can be utilized to measure calcium mobilization:

1. Prepare assay buffer: Hanks balanced salts solution (HBSS) containing 10 mM HEPES, 200 μM $CaCl_2$ and 0.1% bovine serum albumin (BSA), pH 7.4 at 37° C.

2. Reconstitute Fluo-3/AM (Molecular Probes) in dimethyl sulfoxide (DMSO). A stock concentration of 1 mM is appropriate.

3. 48 h after transfection lift adherent cells from flask by adding 2 ml versene (Life Technologies). Rock flask gently to ensure versene completely covers monolayer, then incubate flask for 5 to 10 min at 37° C.

4. Add 8 ml growth medium to flask (to neutralize ethylene bis (oxyethylenitrilo) tetraacetic acid [EGTA]). Pipette solution up and down several times to prepare a homogeneous cell suspension.

5. Transfer cell suspension to a 50-ml conical tube. Pellet cells by centrifuging at 1500 rpm for 5 min. Aspirate growth medium then resuspend cell pellet in 10 ml assay buffer and repeat centrifugation process.

6. Aspirate buffer and resuspend cells in 12 ml fresh assay buffer ensuring that all clumps of cells are well dispersed. Wrap tube in foil to protect contents from light and then add Fluo-3/AM such that final concentration of dye is 1 $\mu$M. Mix thoroughly. For certain cell types (e.g., CHO), it is necessary to include 2.5 mM probenecid in the loading buffer to prevent leakage of dye from the cells.

7. Incubate at 37° C. for 20 min, giving tube a swirl occasionally to prevent cells settling and clumping.

8. Add 36 ml assay buffer, mix well, and incubate at 37° C. for a further 25 min. This should ensure complete hydrolysis of the dye.

9. Centrifuge cells as in step 6. Resuspend cell pellet in 20 ml fresh assay buffer.

10. Perform cell count, centrifuge cells as in step 6 then resuspend in assay buffer to a density of $2 \times 10^6$ cells/ml. Cells should be used within 2 h of loading with Fluo-3.

11. Program Fluoskan reader to read a single column of eight wells repeatedly. Repeat reads on each well can he made every 3.4 s and this time frame is sufficient to allow detection of $Ca^{2+}$ mobilization responses. Set filters to 485 nm excitation and 538 nm emission.

12. Immediately before use, transfer 1.7 ml cell suspension to a 2-ml Eppendorf tube and microfuge briefly to pellet cells. Aspirate buffer and resuspend cell pellet in 1.7 ml fresh assay buffer.

13. Pipette 190 $\mu$l cell suspension into each of the 8 wells in the first column of a 96-well, clear bottom, black-walled plate (Becton Dickinson Labware) and start assay. Take six baseline readings on each well at 3.4 s intervals.

14. Using a multichannel pipette, add test ligands to all eight wells in the column, mixing three or four times, then continue reading plate for 30 readings, again at 3.4 s intervals. Restart readings as quickly as possible following addition of agonist.

15. Repeat steps 13 to 15 for remaining columns on plate. Reader can be set up such that machine will automatically assay column 2 after column 1, etc.

The plate reader will automatically produce a results sheet at the end of the plate run. Fluorescence values are listed for each well at each time point, with plate well reference across the rows (A1, A2, A3, etc.) and time points down the columns, (Note: Fluoroskan automatically inserts empty cells around each value, these cells must be taken into account when designing macros for data analysis.)

Readings are taken every 3.4 s and a 10-s delay is assumed between the sixth and seventh reading per well (i.e., last baseline reading and first reading following agonist addition). Results can be analyzed as follows:

1. Average first six readings to calculate mean baseline value.

2. Determine increase in fluorescence above baseline for each time point following agonist addition and express as a percentage of baseline value.

3. Plot data as change in fluorescence against time.

$Ca^{2+}$ Mobilization Measurements Using FLIPR (Fluorometric Imaging Plate Reader)

The following protocol can be utilized to measure calcium mobilization:

1. 24 h after receptor transfection harvest and plate cells into poly-D-lysine-coated 96-well black-walled/clear bottom microtiter plates (Becton Dickinson Labware) at $3 \times 10^4$ cells per well.

2. After 18 to 24 h aspirate off medium and add 100 $\mu$l of fresh EMEM containing 4 $\mu$M Fluo-3/AM (Molecular Probes; prepare stock solution at 2 mM in DMSO containing 20% pluronic acid), 0.1% BSA, and 2.5 $\mu$M probenecid to each well and incubate for 1 h at 37° C.

3. Aspirate medium and replace with 100 $\mu$l of the same medium, but without Fluo-3/AM, and incubate for 10 min at 37° C. Wash cells three times with a Denley cell washer (Labsystems) with Krebs Ringer Henscleit (KRH; 118 mM NaCl, 4.6 mM KCl, 25 M $NaHCO_3$, 1 mM $KH_2PO_4$, 1.1 mM glucose, 1.1 mM $MgCl_2$) containing 0.1% BSA, 2.5 $\mu$M probenecid, and 20 mM HEPES pH 7.4 (buffer A). After the last wash aspirate down to a final volume of 100 $\mu$l.

4. Prepare plates of potential ligands, tissue extracts, or compound libraries in 96-well polypropylene microplates at three times the final concentration in buffer A and warm to 37° C.

5. Place microplates containing Fluo-3 loaded cells and the ligand plates in FLIPR and monitor. At initiation of the fluorescence recording read measurements every 1 s for 60 s and then every 3 s for the following 60 s. Add agonist (50 $\mu$l) to the cell plate at 10 s and use the maximum fluorescent counts above background after addition of agonist to define maximal activity for that ligand. FLIPR software normalizes fluorescent readings to give equivalent readings for all wells at zero time.

Use of Promiscuous G Proteins with Orphan Receptors

More recently, it has become possible to funnel heterologous signal transduction of GPCRs through a common pathway involving phospholipase C and $Ca^{2+}$ mobilization by co-expression of the receptor with the promiscuous G proteins $G\alpha_{15/16}$ or by co-expression with chimeric G proteins based on Gq. For example, the C3a receptor originally described as an orphan receptor, produces weak or no $Ca^{2+}$ mobilization responses to C3a when expressed in HEK 293 cells. However, when co-expressed with $G\alpha_{16}$, robust responses are seen (FIGS. 4 and 5). Although this cotransfection approach may not be universally successful, it can be a useful technique to promote functional coupling of orphan receptors and to streamline their screening by focusing predominantly on one signal transduction system.

Determination of cAMP Levels via Use of FlashPlate TechnologycAMP Determination Using FlashPlates The following protocol can be utilized to determine cAMP levels:

1. Seed HEK 293 cells into 96-well microtiter plates 24 h prior to assay at a density of $10^5$ cells/well in 100 $\mu$l growth medium. Incubate overnight at 37° C. The wells should reach at least 95% confluency on the following day.

2. Add 10 $\mu$l IBMX (3-isobutyl-1-methylxanthine; final concentration 0.5 mM) and incubate cells for 30 min at 37° C.

3. Add 10 $\mu$l putative ligand immediately followed by 10 $\mu$l growth medium (for determination of cAMP stimulatory responses) or 10 $\mu$l forskolin (for determination of cAMP inhibitory responses) at 30 $\mu$M final concentration. Incubate for 10 min at 37° C.

4. Terminate reaction with the addition of 10 $\mu$l ice cold 5% perchloric acid (PCA).

5. Leave for 1 h at 4° C. to allow equilibrium to be reached before neutralizing samples with 100 $\mu$l 75 mM KOH in 50 mM sodium acetate.

6. Incubate at 4° C. for at least 1.5 h to ensure neutralization is complete and allow sedimentation of the precipitate before transferring samples into cAMP [$^{125}$I] Flash-Plates (NEN Life Sciences; Catalogue no. SMP001), taking care not to disturb the sediment.

7. Typically for HEK 293 Cells, transfer 10 to 40 μl of neutralized sample to FlashPlates for assay. Reconstitute kit reagents as per the manufacturer's instructions and make sample volume up to 100 μl in FlashPlates with assay buffer.

8. Add 100 μl [$^{125}$I] cAMP working tracer, seal plate, and incubate overnight at 4° C. prior to counting.

FIG. 4 shows $Ca^{2+}$ mobilization responses of the C3a receptor expressed with and without the promiscuous G protein $G\alpha_{16}$. Each square represents responses as determined simultaneously via FLIPR from an individual microtiter plate well of cells. The y axis in each square corresponds to intracellular calcium levels and the x axis corresponds to time. The left-hand response of each trace corresponds to challenge with C3a (or buffer) as indicated; the right-hand response of each trace corresponds to challenge with 200 μM muscarine as an internal control for each well. Columns A–D were generated using HEK 293 cells transfected with C3a receptor and columns E–H were generated using cells transfected with both C3a receptor and $G\alpha_{15}$. Quantitation of these data is presented in FIG. 5.

FIG. 5 shows calcium mobilization induced by C3a in HEK 293 cells transiently transfected with C3a receptor, alone (■) or C3a receptor with $C\alpha_{16}$ (●). The maximum $Ca^{2+}$ response (peak height) following C3a addition to each well, as illustrated in FIG. 4 was used to construct the dose-response curves. Each point in FIG. 5 represents the mean±SEM of eight determinations.

The assay can be used not only to screen for ligands that activate Gs- or Gi-coupled orphan receptors, but also to look for receptors that might be constitutively active. For example, elevated basal cAMP levels can be detected in HEK 293 cells expressing the orphan receptor GPR3, consistent with the constitutive activity reported for this receptor. Such receptors are amenable to screening for compounds with inverse agonist activity which reduce the elevated basal levels of activity, which can then be used as tools to explore the biology of the receptor in vivo.

A "homogeneous" version of the flashplate assay (SMP004) has been developed by NEN Life Sciences. In this format the cells and test substance are added directly to the flashplate, the incubation terminated by a single addition (which includes the radiolabel) and the plate then counted 2 to 24 h later at room temperature. The reduced number of pipetting steps results in a higher throughput. However, a caveat when screening tissue extracts concerns the lack of an acid precipitation step to remove excess proteinaceous material which may thus interfere with the assay.

In summary, the present invention provides methods for evaluating drug candidates whose mechanism of action is as a GPCR receptor agonist. By using the efficacy index to evaluate compounds, the risks of failure from lack of clinical or therapeutic efficacy are minimized. The methods of the present invention have been applied to motilides where both novel compounds and those currently being studied in clinical trials are evaluated.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLE 1

Co-Expression of a GPCR and Aequorin in a Cell Line and Potency Measurement

A gene encoding the target receptor is cloned and placed into a mammalian expression vector such as pcDNA3.1. The gene may be synthetic or naturally derived. Next, pmtAEQ, an aequorin expression plasmid available from Molecular Probes, and the receptor expression construct are transfected into HEK293 cells using a commercially available transfection kit such as Lipofectamine Plus (Gibco BRL). At this point, a stable cell line may be selected from the transfection mix using common techniques, or the heterologous mixture obtained from transient transfection may be used directly. Cells expressing aequorin and the target receptor are then harvested and soaked in a solution of phosphate buffer saline containing 0.1 g/L $CaCl_2$, 0.1 g/L $MgCl_2$, 36 mg/L pyruvate, and 1 g/L glucose (in phosphate buffer solution ("PBS")) with 2.5 μM coelenterazine f and 300 uM reduced glutathione for 0.5–4 hours. The cells are washed and diluted to 500,000 cells/mL in PBS. One hundred microliters of varying concentrations of a test agonist are placed in the wells of a 96-well white plastic assay plate. A 100 uL aliquot of cells is added to each well, and following each addition, the integrated luminescence is measured for 30–60 seconds and is taken as the agonist response. Next, 100 uL of 1% triton X-100 in PBS is injected into each well, and the integrated luminescence is measured a second time over 30–60 seconds and is taken as the triton response. A value F is calculated as equaled to the agonist response divided by the sum of the agonist response and the triton response. F is plotted versus the agonist concentration, and the data is fit to a rectangular square hyperbola to obtain the $EC_{50}$ value for the compound.

EXAMPLE 2

Desensitization Measurement in a Cell Line Coexpressing GPCR and Aequorin

Cells expressing a target receptor and aequorin are grown, harvested and counted. Cells are then incubated in PBS with varying concentration of test compound in a 1 mL reaction containing 500,000 cells. The reaction is incubated at 37° C. for a set amount of time (initially varied to determine the time dependence of desensitization). The reaction is diluted, cells are separated from the test compound by centrifugation, resuspended (in PBS containing 0.1 g/L $CaCl_2$, 0.1 g/L $MgCl_2$, 36 mg/L pyruvate, and 1 g/L glucose) and recentrifuged to wash away any remaining test compound. To reconstitute the aequorin cofactor, the cells are then resuspended in 5 mL of PBS containing 2.5 uM coelenterazine f and 300 uM reduced glutathione, and incubated at 37° C. for 30–45 minutes. The cells are centrifuged once more, then resuspended in 800 uL of PBS for assay.

100 μL of cells are placed in the well of a 96-well white assay plate, and an amount of an agonist known to saturate the receptor is added. Each aliquot of cells, pretreated with a different concentration of test compound, is challenged with the agonist and the integrated luminescence is measured over 30–60 seconds ("agonist response"). Next, 100 uL of 1% triton X-100 in PBS is injected into the well and the integrated luminescence is measured over 30–60 seconds ("triton response"). The fractional activation of the receptor is then expressed as F=agonist response/(agonist response+triton response). F is then plotted as a function of the test compound, and the resulting curve is fit to a rectangular square hyperbola to obtain an $IC_{50}$ value for desensitization of the receptor by the test compound.

EXAMPLE 3
Expression of the Motilin Receptor and Aequorin

A synthetic gene encoding the motilin receptor was designed using common methods based upon the sequence of the naturally occurring human motilin gene. An error in the synthesis was corrected to give Kos127-42-61, a pUC derived vector containing a synthetic gene encoding the motilin receptor. The HindIII/EcoRI fragment of pkos127-42-61, containing a fully sequenced synthetic gene encoding the human motilin receptor and an upstream Kozak sequence was subcloned into the pcDNA3.1(+) expression vector. The resulting plasmid construct (pkos127–159) was verified by restriction analysis and DNA sequencing.

HEK293 cells (ATCC CRL-1573) were grown to ~95% confluence in T175 flasks at 37° C. in an atmosphere containing 5% $CO_2$. Each T175 flask was transfected with a total of 11.5 ug of DNA using the Lipofectamine Plus reagents and the protocol supplied by the manufacturer. For transient transfections, the ratio of pkos127–159 ("motilin receptor DNA") to pmtAEQ ("aequorin DNA") was 10:1, while transfections performed to generate stable cell lines used a receptor DNA:aequorin DNA ratio of 1:10. Transiently transfected cells were harvested 18–22 hours post transfection by removing the medium and treating the layer of cells with 5 mL of Trypsin-EDTA for 20 minutes at 37° C. The trypsin reaction was quenched with 50 mL of MEMalpha medium containing 10% fetal bovine serum, and the cell suspension was triturated with a 10 mL pipette. The cells were harvested by centrifugation and washed with 50 mL of PBS. A 50 uL aliquot was mixed with 50 uL of Trypan blue (0.4% v/v) and counted using a hemocytometer.

For the generation of stable cell lines, cells were allowed to recover for 3 days following the transfection, at which time the medium was replaced with fresh medium containing 800 ug/mL G418. A flask of non-transfected cells was also incubated in the presence of 800 ug/mL G418. The medium was changed 7 days post transfection, and by 10 days following transfection, ~80% of the transfected cells had died, and no viable cells were visible in the flask containing the non-transfected control. Two weeks after transfection, single, well separated colonies were visible and could be circled with a marker pen. Medium was aspirated, replaced with a thin layer of PBS, and clones were isolated by scraping the area of the circled colony with a pipette tip while simultaneously drawing PBS (and cells) into the pipette tip. Clones were dispensed into 24 or 6-well tissue culture clusters in MEMalpha containing 800 ug/mL G418. Colonies were amplified for ~2 weeks, then split into duplicate wells containing MEMalpha medium and 200 ug/mL G418.

EXAMPLE 4
Motilin Receptor Activation Assay

Flasks containing HEK293 cells either transiently or stably expressing the motilin receptor and aequorin were used in receptor activation assays. Cells were grown to 80–100% confluence in T175 flasks containing MEMalpha medium with 10% v/v fetal bovine serum, harvested by trypsinization, and counted using a hemocytometer. Trypan blue staining was used to confirm viability of >80% of the cells. The cells were resuspended in 30 mL of prewarmed (37° C.) PBS and 2.5 uM coelenterazine f (from a 2.5 mM stock in methanol) and 300 uM reduced glutathione. Reconstitution of the coelenterazine f cofactor into aequorin proceeded for 1–4 hours at 37° C. in an atmosphere containing 5% $CO_2$, at which time the cells were harvested by centrifugation, washed with 2×50 mL prewarmed PBS, resuspended in prewarmed PBS to a concentration of ~$5 \times 10^5$ to $10^6$ cells/mL, and maintained at 37° C. for the duration of the assay.

Stock solutions (20 mM) of test compounds were made in ethanol and diluted 100-fold into PBS. Motilin was dissolved in water to a concentration of 185 uM. Serial 10-fold dilutions of motilin and test compounds were made in PBS to generate a series of stock solutions ranging from $10^{-4}$ to $10^{-11}$ M, and triplicate 100 uL aliquots were placed in the wells of a white, opaque 96-well assay plate. Control wells were also included which contained only PBS or 1% v/v ethanol in PBS. The plate was loaded into a Wallac Victor 1420 multilabel counter equipped with two reagent injectors. One of the injectors was used to add 100 uL of the cell suspension (~$5 \times 10^4$ to $10^5$) to each well, and the bioluminescence response was measured over the course of 30–60 seconds. A second measurement was then made following injection of 100 uL of 1% triton X-100 in PBS. The F value of the cells to each test compound was calculated using equation 1, and data were fit to equation 2 to obtain $EC_{50}$ values for the test compounds.

$F$=agonist response/(agonist response+triton response). Equation 1

$F$=Basal response+(total change*[agonist])/
($EC_{50}$+[agonist]). Equation 2

EXAMPLE 5
Motilin Receptor Desensitization Assay

HEK293 cells stable expressing the motilin receptor and aequorin were grown to near confluence, harvested by trypsinization, stained with trypan blue and counted, then diluted to ~$5 \times 10^5$ to $10^6$ cells/mL. Cells were then incubated with varying concentrations of test compound in a 1 mL reaction containing ~500,000 cells. The reaction was incubated at 37° for a set amount of time (initially varied for a single concentration of compound to determine the time dependence of desensitization). The reaction was diluted, cells were separated from the test compound by centrifugation, resuspended in PBS and recentrifuged to wash away any remaining test compound. The cells were then resuspended in 5 mL of PBS containing 2.5 uM coelenterazine f and 300 uM reduced glutathione, and incubated at 37° C. for 30–45 minutes to reconstitute aequorin's essential cofactor. The cells were centrifuged once more, then resuspended in 800 uL of PBS for assay.

A 100 uL aliquot of cells was placed in the well of a 96-well white assay plate, and a Victor multilabel counter equipped with a reagent injection system was used to add 100 uL of 1.85 uM motilin. Each aliquot of cells, pretreated with a different concentration of test compound, was challenged with motilin and the integrated luminescence was measured over 30–60 seconds ("agonist response"). Next, 100 uL of 1% triton X-100 in PBS was injected into the well and the integrated luminescence was measured over 30–60 seconds ("triton response"). The F value of the receptor was expressed as F=agonist response/(agonist response+triton response). F was plotted as a function of the test compound, and the resulting curve was fit to a rectangular square hyperbola to obtain an $IC_{50}$ value for desensitization of the receptor by the test compound.

EXAMPLE 6
Method of Making 13-propyl-6-deoxyerythronolide B (13-propyl-6-dEB)

A 1 mL vial of the CH999/pJRJ2 (*Streptomyces coelicolor* that contains a PKS in which the ketosynthase domain of module 1 has been inactivated by mutation) working cell bank is thawed and the contents of the vial are added to 50 mL of Medium 1 in a 250 mL baffled flask.

Medium 1 comprises 45 g/L cornstarch; 10 g/L corn steep liquor; 10 g/L dried, inactivated brewers yeast; and 1 g/L CaCO$_3$. This solution is sterilized by autoclaving for 90 minutes at 121° C. After sterizilization, 1 mL/L of sterile filtered 50 mg/ml thiostrepton in 100% DMSO and 1 mL/L autoclaved 100% antifoam B silicon emulsion (J. T. Baker) are added prior to use.

The flask is placed in an incubator/shaker maintained at 30±1° C. and 175±25 RPM for 48±10 hours. The 50 mL culture is then added to a 2.8 L baffled flask containing 500 mL of Medium 1. This flask is incubated in an incubator/shaker at 30±1° C. and 175±25 RPM for 48±10 hours. The 500 mL culture is than used to inoculate a 10 L fermenter containing 5 L of Medium 1. The fermenter is controlled at 30° C., pH 6.5 by addition of 2.5 N H$_2$SO$_4$ and 2.5 N NaOH, agitation rate 600 RPM, and air flow rate 1–2 LPM. Foam is controlled by the addition of a 50% solution of Antifoam B as needed. The fermenter culture is allowed to grow under these conditions for 24±5 hours.

A 150 L fermenter is prepared by sterilizing 100 L of Medium 1 at 121° C. for 45 minutes. After the growth period, the contents from the 10 L fermenter are aseptically added to a 150 L fermenter. The fermenter is controlled at 30° C., pH 6.5 by addition of 2.5 N H$_2$SO$_4$ and 2.5 N NaOH, dissolved oxygen ≧80% air saturation by agitation rate (500–700 RPM), air flow rate (10–50 LPM), and/or back pressure control (0.1–0.4 bar). Foam is controlled by the addition of a 50% solution of Antifoam B as needed.

At 35+5 hours, after dissolved oxygen has reached a minimum and CO$_2$ content in fermenter offgas has reached a maximum, (2S, 3R)-2-methyl-3-hydroxypentanoyl-N-acetylcysteamine (propyl diketide) is added to a final concentration of 2 g/L. Propyl diketide is prepared by solubolizing in dimethyl sulfoxide at a ratio of 2:3 (diketide to DMSO) and then filter sterilized (0.2 μm, nylon filter). Production of 13-propyl-6-deoxyerythonolide B (13-propyl-6-dEB) ceases on day 8 and the fermenter is harvested. The fermentation broth is centrifuged at 20,500 g in an Alpha Laval AS-26 centrifuge. The product is predominantly in the centrate; the centrifuged cell mass is discarded.

After centrifugation, solid phase extraction is performed using HP20 resin (Mitsubishi). Column size is selected based on centrate volume and titer, so that the loading capacity of 15 g 13-propyl-6-dEB per liter HP20 resin is not exceeded. The centrifuged broth is passed through the resin bed at a linear flow rate of 300±20 cm/h. The pressure on the column should not exceed 15 psi. The resin is then washed with 2 column volumes (CV) of water and then 2 CV of 30% methanol, each at a rate of 300±20 cm/h. 13-propyl-6-dEB is eluted using 7–10 CV 100% methanol at a rate of 300±20 cm/h. During elution, fractions of 1 CV are collected. The fractions are then analyzed, and those containing product are combined to yield a product pool containing >95% of the original 13-propyl-6-dEB in the centrifuged broth. The product pool is reduced to solids using rotary evaporation. Product purity at this stage is 5–35%. Methanol-insoluble material is removed from the product pool by suspending the solids in 3 L 100% methanol per 100 L original broth volume, mixing for 20 minutes, and filtering.

The final purification step is chromatography using HP20SS resin (Mitsubishi). Column size is selected based on amount of product, so that the loading capacity of 15 g 13-propyl-6-dEB per liter HP20SS resin is not exceeded. The filtered methanol solution is diluted by adding an equal volume of water. The 50% methanol solution is passed through the resin bed at a linear flow rate of 300±20 cm/h. The column is then washed with 2 CV of 50% methanol at a rate of 300±20 cm/h. Product is eluted using 12 CV 70% methanol at a rate of 300±20 cm/h. During elution, fractions of 1 CV are collected. The fractions are then analyzed, and those containing >50 mg/L 13-propyl-6-dEB and having >20% chromatographic purity are combined. The product pool is reduced to solids using rotary evaporation. Product purity at this stage is >65% and is suitable for bioconversion to the appropriate erythromycin.

EXAMPLE 7
Method of Making 13-propyl erythromycin A

A 1 mL vial from working cell bank K39-14V (an eryA mutant of S. erythraea that is incapable of producing 6-dEB) is thawed and the contents of the vial are added to 50 mL of Medium 2 in a 250 mL baffled flask.

Medium 2 comprises 16 g/L cornstarch; 10 g/L corn dextrin; 15 g/L soy meal flour; 4 g/L CaCO$_3$; 5 g/L corn steep liquor, 6 g/L soy bean oil; 2.5 g/L NaCl; and 1 g/L (NH$_4$)$_2$SO$_4$. This solution is sterilized by autoclaving for 60 minutes at 121° C. and 1 mL/L autoclaved 100% antifoam B silicon emulsion (J. T. Baker) is added prior to use.

The flask is placed in an incubator/shaker maintained at 34±1° C. and 175±25 RPM for 48±10 hours. The 50 mL culture is then added to a 2.8 L baffled flask containing 500 mL of Medium 2. The flask is incubated in an incubator/shaker at 34+1° C. and 175±25 RPM for 48±10 hours. The 500 mL culture is than used to inoculate a 10 L fermenter containing 5 L of Medium 2. The fermenter is controlled at 34° C., pH 7.0 by addition of 2.5 N H$_2$SO$_4$ and 2.5 N NaOH, agitation rate 600 RPM, and air flow rate 1–2 LPM. Foam is controlled by the addition of a 50% solution of Antifoam B as needed. The fermenter culture is allowed to grow under these conditions for 24±5 hours.

A 150 L fermenter is prepared by sterilizing 100 L of Medium 3 at 121° C. for 45 minutes. Medium 3 comprises 17.5 g/L cornstarch; 16 g/L corn dextrin; 16.5 g/L soy meal flour; 4 g/L CaCO$_3$; 6 g/L corn steep liquor; 3 g/L soy bean oil; 3.5 g/L NaCl; and 1 g/L (NH$_4$)$_2$SO$_4$. After the growth period, the contents from the 10 L fermenter are aseptically transferred to the 150 L fermenter. The fermenter is controlled at 34° C., pH 7.0 by addition of 2.5 N H$_2$SO$_4$ and 2.5 N NaOH, dissolved oxygen ≧80% air saturation by agitation rate (500–700 RPM), air flow rate (15–50 LPM), and/or back pressure control (0.1–0.4 bar). Foam is controlled by the addition of a 50% solution of Antifoam B.

At 24±5 hours a 58–60 mL/hour 15% dextrin (w/v) feed is initiated. The dextrin solution is continuously mixed during the feed period. At 24±5 hours 25 grams of 13-propyl-6dEB are added to the fermenter. The 13-propyl-6-dEB is prepared by solubolizing 25 grams of 13-propyl-6-dEB in 400–600 mL of 100% ethanol and filtering (0.2 μm, nylon filter). Conversion of 13-propyl-6-dEB to 13-propyl-erythromycin A ceases after 60±10 hours and the fermenter is harvested. The fermentation broth is centrifuged at 20,500 g in an Alpha Laval AS-26 centrifuge. The product is predominantly in the centrate; the centrifuged cell mass is discarded.

After centrifugation, solid phase extraction is performed using HP20 resin (Mitsubishi). Column size is selected based on centrate volume and titer, so that the loading capacity of 15 g 13-propyl-erythromycin A per liter HP20 resin is not exceeded. The centrifuged broth is adjusted to pH 9, then passed through the resin bed at a linear flow rate of 275±25 cm/h. The pressure on the column should not exceed 15 psi. The resin is then washed with 1 column volume (CV) of water at a rate of 275±25 cm/h. 13-propyl-6-dEB is eluted using 5 CV 100% methanol at a rate of 275±25 cm/h. During elution, fractions of 1 CV are collected. The fractions are then analyzed, and those containing product are combined to yield a product pool. The product pool is reduced to solids using rotary evaporation.

Methanol-insoluble material is removed from the product pool by suspending the solids in 1 L 100% methanol per 100 L original broth volume, adjusting to pH 9, and filtering. The product pool (filtrate) is reduced to solids using rotary evaporation.

13-propyl-erythromycin A is extracted from the product pool (solids) by adding 2 L 4:1 hexane:acetone per 100 L original broth volume, mixing for 20 minutes, and filtering. The remaining solids are extracted the same way two more times and filtrates are combined. The product pool is reduced to solids using rotary evaporation.

The final purification step is chromatography using HP20SS resin (Mitsubishi). Column size is selected based on amount of product, so that the loading capacity of 15 g 13-propyl erythromycin A per liter HP20SS resin is not exceeded. The solids from the previous steps are dissolved in 1 L methanol per 100 L original broth volume, and an equal volume of water is added. The 50% methanol solution is passed through the resin bed at a linear flow rate of 275±25 cm/h. The column is then washed with 1 CV of 50% methanol, then 3 CV 60% methanol, each at a rate of 275±25 cm/h. Product is eluted using 3 CV 70% methanol, then 10 CV 75% methanol, each at a rate of 275±25 cm/h. During elution, fractions of 1 CV are collected. The fractions are then analyzed, and those containing 13-propyl-erythromycin A are combined. The product pool is reduced to solids using rotary evaporation.

EXAMPLE 8
8,9-anhydro-6,9-hemiacetal (enol ether) formation

A solution of erythromycin (100 mg) in anhydrous acetonitrile (2 mL) is treated with dichloroacetic acid (0.015 mL) under inert atmosphere until thin-layer chromatography reveals disappearance of starting material (2 days). The reaction mixture is concentrated, redissolved in 50 mL of dichloromethane, and washed with saturated NaHCO$_3$. The organic phase is dried over Na$_2$SO$_4$, filtered, and concentrated to give the crude product. Silica gel chromatography (acetone+2% Et$_3$N, hexanes) gives the pure product. Other compounds of the invention are formed by substituting the corresponding erythromycin derivative for the erythromycin in the above procedure.

An exemplary NMR data for one of the compounds of the present invention, 8,9-anhydroerythromycin A 6,9-hemiacetal is as follows. $^{13}$C-NMR (CDCl$_3$): δ 178.2, 151.7, 102.9, 101.4, 94.6, 85.5, 80.1, 78.2, 78.1, 76.3, 75.3, 73.0, 70.8, 70.1, 68.8, 65.8, 65.6, 49.5, 44.7, 43.2, 42.6, 40.3, 34.6, 30.5, 28.7, 26.2, 21.5, 21.3, 21.0, 18.2, 16.1, 15.0, 13.4, 11.9, 11.4, 10.8, 8.6.

EXAMPLE 9
Hydrogenation of 8,9-anhydroerythromycin 6,9-hemiacetals to (8S,9R)-9-deoxo-6,9-epoxyerythromycins A solution of the 8,9-anhydroerythromycin 6,9-hemiacetal (0.55 mmol; Example 8) in 24 mL of glacial acetic acid is treated with difluoroacetic acid (0.1 mL) and platinum oxide (0.4 g). The mixture is shaken under 4 atm of hydrogen at ambient temperature for 3 hours, or until consumption of starting material as indicated by thin-layer chromatography. Ammonium acetate (0.3 g) is added, the mixture is stirred for 15 minutes, then filtered and concentrated. The residue is dissolved in dichloromethane, washed with sat. NaHCO$_3$, dried over Na$_2$SO$_4$, filtered, and evaporated. Silica gel chromatography (acetone+2% Et$_3$N, hexanes) gives the pure product.

EXAMPLE 10
Ring Contraction of 14-Membered to 12-Membered Macrolides

A solution of the 8,9-anhydroerythromycin 6,9-hemiacetal derivative (1 mmol; Example 8) and potassium carbonate (200 mg) in methanol (50 mL) is heated at reflux until thin-layer chromatographic analysis reveals the reaction has reached equilibrium. The mixture is evaporated to dryness, then dissolved in CH$_2$Cl$_2$ and chromatographed on silica gel. Both 14-membered enol ethers and 9-deoxo-6,9-epoxides are converted into their 12-membered macrolide counterparts using this procedure. Those derivatives containing 2'-O-acetates, 4"-O-formates, 4"-O-(2,2,2-trichloroethoxycarbonyl), or 11,12-cyclic carbonates are deprotected during this process.

EXAMPLE 11
3'-N-desmethyl erythromycin Derivatives

Sodium acetate trihydrate (300 mg) and iodine (116 mg) are added sequentially to a solution of erythromycin (300 mg) in 3 mL of methanol. The reaction mixture is exposed to a 120 W flood lamp and stirred until complete reaction is determined by thin-layer chromatographic analysis. Excess reagents are quenched by addition of saturated sodium thiosulfate solution, and the volatiles are removed under reduced pressure and the mixture is diluted with dichloromethane. The organic phase is washed with saturated NaHCO$_3$, dried over Na$_2$SO$_4$, filtered, and concentrated to give the crude product. Silica gel chromatography (acetone+2% Et$_3$N, hexanes) gives the pure product.

The 3'-N-desmethyl-8,9-anhydroerythromycin 6,9-hemiacetals are prepared by substituting the 8,9-anhydroerythromycin 6,9-hemiacetals for the erythromycin in the above procedure.

EXAMPLE 12
3'-N-desmethyl-3'-N-alkyl-erythromycin Derivatives

A solution of the 3'-N-desmethyl-erythromycin derivative (0.5 mmol; Example 11) in acetonitrile (6 mL) is treated with diisopropylethylamine (0.23 mL) and the desired alkylating agent (0.6 mmol) and stirred at 40–80° C. under inert atmosphere until consumption of the erythromycin starting material as determined by thin-layer chromatographic analysis. The reaction mixture is concentrated under vacuum and redissolved in dichloromethane, washed with saturated NaHCO$_3$, dried over Na$_2$SO$_4$, filtered, and concentrated to give the crude product. Silica gel chromatography (acetone+2% Et$_3$N, hexanes) gives the pure product.

Alkylating agents useful in this procedure include ethyl iodide, benzyl bromide, 2-iodopropane, 4-bromo-1-butene, allyl bromide, propargyl bromide, or sec-butyl iodide, or the corresponding trifluoromethanesulfonates, which give rise to the 3'-N-ethyl, isopropyl, butenyl, allyl, propargyl, or sec-butyl derivatives, respectively.

3'-N-desmethyl-3'-N-alkyl-8,9-anhydroerythromycin 6,9-hemiacetal is prepared by substituting 3'-N-desmethyl-8,9-anhydroerythromycin 6,9-hemiacetal (Example 11) for the 3'-N-desmethyl-erythromycin in the above procedure.

EXAMPLE 13
2'-O-acetyl-erythromycin

A 0° C. solution of erythromycin (13.4 mmol) in ethyl acetate (50 mL) is treated with acetic anhydride (1.4 mL) for 30 minutes, then kept for 4 hours at ambient temperature. The mixture is quenched with sat. NaHCO$_3$, and extracted with ethyl acetate. The extracts are combined, dried over MgSO4, filtered, and concentrated to dryness under reduced pressure to yield the crude product. The product is either crystallized or purified by silica gel chromatography. NMR data follows for one of the compounds of the present invention, 2'-O-acetyl-13-propyl erythromycin A, that was crystallized from acetonitrile. $^{13}$C-NMR (CDCl$_3$): δ 222.3, 175.4, 170.0, 100.9, 96.1, 83.4, 79.7, 75.1, 75.0, 74.5, 72.7, 71.7, 68.9, 68.4, 65.7, 63.6, 49.4, 45.2, 44.8, 40.7, 39.2, 38.1, 37.8, 35.0, 31.6, 30.3, 30.2, 27.0, 22.6, 21.5, 21.5, 21.2, 19.5, 18.6, 18.1, 16.3, 15.8, 14.1, 14.0, 12.0, 9.0.

EXAMPLE 14
2'-O-acetyl-4"-deoxy-erythromycin

Step 1. A mixture of 2'-O-acetyl-erythromycin (3.5 mmol; Example 13), thiocarbonyldiimidazole (1 g), and 4-dimethylaminopyridine (0.67 g) in 100 mL of CH$_2$Cl$_2$ is stirred overnight at ambient temperature. The mixture is treated with 150 mL of sat. NaHCO$_3$, and the organic phase is then washed with water, dried over MgSO$_4$, filtered, and evaporated. The product 4"-O-thiocarbonylimidazolide is crystallized.

Step 2. The product from Step 1 is dissolved in 60 mL of toluene and heated to 98° C. Tributyltin hydride (1.9 mL) is added followed by 2,2'-azobisisobutyronitrile (60 mg) and heating is continued for 35 minutes. The mixture is concentrated under reduced pressure. The oily residue is dissolved in 340 mL of acetonitrile, washed with 5 portions of hexanes, and concentrated to yield the crude product. Purification by silica gel chromatography yields the pure product. NMR data follows for one of the compounds of the present invention, 2'-O-acetyl-4"-deoxyerythromycin A: $^{13}$C-NMR: δ 222.0, 175.6, 170.0, 100.4, 96.8, 83.2, 79.0, 74.8, 74.6, 71.7, 70.5, 68.9, 67.9, 63.2, 61.4, 49.2, 45.3, 45.1, 44.7, 40.7, 38.9, 37.9, 34.1, 30.7, 26.8, 25.5, 25.2, 22.2, 21.9, 21.5, 21.2, 18.2, 16.3, 15.9, 12.0, 10.6, 9.1.

EXAMPLE 15
2'-O-acetyl-4"-O-(2,2,2,-trichloroethoxycarbonyl)-erythromycin

A solution of 2'-O-acetyl-erythromycin (100 mmol; Example 13) and 4-dimethylaminopyridine (49.0 g) in CH$_2$Cl$_2$ (500 mL) is cooled to −78° C. and stirred under inert atmosphere. Trichloroethyl chloroformate (50 mL) is added dropwise, and the mixture is stirred for 48 hours. After warming to ambient temperature, the mixture is washed with cold phosphate buffer (1: v/v mix of 5% KH$_2$PO$_4$ and 1% K$_2$HPO$_4$) followed by brine, dried over MgSO$_4$, filtered, and concentrated. The product is purified by crystallization or silica gel chromatography.

EXAMPLE 16
2'-O-acetyl-erythromycin A 11,12-cyclic carbonate

A mixture of 2'-O-acetyl-4"-deoxy-erythromycin A (1.6 mmol; Example 14), 1,1-carbonyldiimidazole (1.64 g), and 4-dimethylaminopyridine (0.41 g) in 13 mL of CH$_2$Cl$_2$ is warmed gently to dissolve the solids, then allowed to stir overnight at ambient temperature. Saturated NaHCO$_3$ (20 mL) is added and stirred for 15 minutes, then the mixture is extracted with CH$_2$Cl$_2$. The extract is washed with water, dried over MgSO$_4$, filtered, and evaporated to yield 2'-O-acetyl-4"deoxy-erythromycin A 11,12-cyclic carbonate.

2'-O-acetyl-4"-O-(2,2,2-trichloroethoxycarbonyl) erythromycin A 11,12-cyclic carbonate is made by substituting 2'-O-acetyl-4"-O-2,2,2-trichloroethoxycarbonyl)-erythromycin A (Example 15) for 2'-O-acetyl-4"-deoxy-erythromycin A in the above procedure.

EXAMPLE 17
(9S)-9-dihydro-erythromycins

A solution of 2'-O-acetyl-4"-deoxy-erythromycin A 11,12-cyclic carbonate (0.5 mmol; Example 16) in 10 mL of ethanol is treated with sodium borohydride (200 mg), and the reaction is monitored by thin-layer chromatography. When the reaction is ca. 80% complete, 0.5 M phosphate buffer (50 mL) is added and the mixture is extracted with CH$_2$Cl$_2$. The extract is washed with phosphate buffer, dried over MgSO$_4$, filtered, and evaporated. The product, (9S)-2'-O-acetyl-4"-deoxy-9-dihydro-erythromycin A 11,12-cyclic carbonate, is purified by silica gel chromatography. NMR data follows for one of the compounds of the invention, (9S)-2'-O-acetyl-9-dihydroerythromycin A 11,12-cyclic carbonate: $^{13}$C-NMR: δ 175.8, 169.9, 153.8, 100.1, 96.7, 85.3, 82.3, 81.1, 80.0, 77.7, 76.5, 74.6, 71.7, 70.6, 68.6, 62.9, 61.8, 49.1, 45.3, 44.7, 42.3, 40.7, 34.5, 34.2, 33.6, 30.9, 25.5, 25.1, 22.9, 21.5, 21.4, 21.0, 20.1, 14.5, 14.4, 14.3, 10.7, 9.2.

(9S)-2'-O-acetyl-9-dihydro-erythromycin A is made by substituting 2'O-acetyl-4"-O-(2,2,2-trichloroethyoxycarbonyl)-erythromycin A 11, 12-cyclic carbonate (Example 16) instead of 2'-O-acetyl-4"-deoxy-erythromycin A 11, 12-cyclic carbonate.

EXAMPLE 18
9-deoxo-6,9-epoxy-erythromycins

A solution of (9S)-2'-O-acetyl-4"-deoxy-9-dihydro-erythromycin A 11,12-cyclic carbonate (1 mmol; Example 17) in 25 mL of CH$_2$Cl$_2$ at 0° C. is treated with pyridine (0.26 mL; Example 21) and trifluoromethanesulfonic anhydride (0.35 mL). After 30 minutes, sat. NaHCO$_3$ is added and the mixture is extracted with CH$_2$Cl$_2$. The extract is washed with water, dried over MgSO$_4$, filtered, and evaporated. The product, (8R, 9R)-2'-O-acetyl-4"-deoxy-9-deoxo-6,9-epoxy-13-desethyl-13-R-erythromycin A, is isolated by silica gel chromatography.

EXAMPLE 19
Removal of 2'-O-acetate and 11,12-cyclic carbonate Protection

A solution of the 2'-O-acetyl-erythromycin 11, 12-cyclic carbonate (1 mmol; Example 16) in 25 mL of methanol is treated with potassium carbonate (3 mmol). Upon completion of the reaction, the mixture is evaporated, and the residue is dissolved in CH$_2$Cl$_2$. The extract is washed with water, dried over MgSO4, filtered, and evaporated. The product is isolated by silica gel chromatography.

EXAMPLE 20
Removal of 4"-O-(2,2,2-trichloroethoxycarbonyl) Protection

Samarium iodide is prepared by stirring a solution of samarium (3.43 mmol) and iodine (3.09 mmol) in 40 mL of tetrahydrofuran at reflux for 2.5 hours. Upon cooling to ambient temperature, 10 mg of NiI$_2$ is added and the mix is cooled to −78° C. A solution of the 4"-O-(2,2,2-trichloroethoxycarbonyl)-protected erythromycin derivative (0.386 mmol) in 10 mL of tetrahydrofuran is added, and the mix is stirred for 1 hour at −78° C. The reaction is quenched by addition of sat. NaHCO$_3$, warmed to ambient temperature, and extracted with ether. The extract is dried over MgSO$_4$, filtered, and evaporated. The product is purified by silica gel chromatography.

EXAMPLE 21
12-membered macrolide 12,13-epoxide

A solution of the 12-membered macrolide (1 mmol; Example 10) in CH$_2$Cl$_2$ is added to a solution of bis[α, α-bis(trifluoromethyl)benzenemethanolato-]-diphenylsulfur (1.5 g) in CH$_2$Cl$_2$. After 45 minutes, a second portion of sulfurane (0.75 g) is added, and the reaction is continued for an additional 30 minutes. The mixture is poured into ethyl acetate and 5% aqueous NaHCO$_3$ is added until the pH of the aqueous phase reaches 7. The organic phase is separated, and the aqueous phase is extracted three times with ethyl acetate. The organic solutions are combined, washed with aq. NaCl, dried over MgSO$_4$, filtered, and evaporated. The product is isolated by silica gel chromatography.

EXAMPLE 22
Erythromycin A lactams

A solution of the epoxide (1 mmol; Example 21) and ammonium chloride (2 g) in 7 N methanolic ammonia (100 mL) is placed in a sealed bomb and heated at 100° C. for 4 days. The bomb is cooled and opened, and the mixture is evaporated to dryness. The product is isolated by silica gel chromatography.

EXAMPLE 23
N-alkyl-Erythromycin A lactams

A solution of the epoxide (1 mmol; Example 21), the alkylamine R—NH$_2$ (0.5 mol), and conc. HCl (5 mmol) is placed in a sealed bomb and heated at 100° C. for 4 days. The bomb is cooled and opened, and the mixture is evaporated to dryness. The product is isolated by silica gel chromatography.

EXAMPLE 24
3'-N-desmethyl-erythromycin lactam 9-deoxo-6,9-epoxy-erythromycin A lactam (1 mmol; Example 22) and sodium acetate trihydrate (690 mg) in 10 mL of 80:20 methanol/water is heated to 47° C. and treated with iodine (257 mg). The pH is maintained in the range of 8–9 by addition of 1 N NaOH when needed. After 2 hours, the colorless mixture is poured into water and adjusted to pH 10, then extracted with CH$_2$Cl$_2$. The extract is washed sequentially with aq. Na$_2$S$_2$O$_3$ and brine, then dried over MgSO$_4$, filtered, and evaporated. The product is isolated by silica gel chromatography.

EXAMPLE 25
Alternate Preparation of 3'-N-desmethyl-erythromycin lactam

A solution of -deoxo-6,9-epoxy-13-erythromycin A lactam (1 mmol; Example 22) in 40 mL of anhydrous CH$_3$CN at 0° C. is treated with N-iodosuccinimide (270 mg) in small portions. After addition, the mixture is kept at ambient temperature for 12 hours. The mixture is diluted with ethyl acetate and washed sequentially with aq. NaHSO$_3$, 5% Na$_2$CO$_3$, and brine, then dried over MgSO$_4$, filtered, and evaporated. The product is isolated by silica gel chromatography.

EXAMPLE 26
3'-N-desmethyl-3'-N-alkyl-erythromycin lactam

A solution of the 3'-N-desmethyl-9-deoxo-6,9-epoxy-erythromycin A lactam (1 mmol; Examples 24 and 25) in CH$_3$CN (10 mL) is treated with solid NaHCO$_3$ (420 mg) and an alkylating agent (e.g., alkyl halide or alkyl sulfonate) (1.1 mmol) with stirring for 2 days at ambient temperature. The mixture is diluted with ethyl acetate and washed sequentially with sat. NaHCO$_3$ and brine, then dried with MgSO$_4$, filtered, and evaporated. The product is isolated by silica gel chromatography.

EXAMPLE 27
Alternate Preparation of 3'-N-desmethyl-3'-N-alkyl-erythromycin lactam A solution of the 3'-N-desmethyl-9-deoxo-6,9-epoxy-erythromycin A lactam (2 mmol; Examples 24 and 25) and an aldehyde or ketone (8 mmol) in 20 mL of methanol is treated with acetic acid (0.46 mL) and sodium cyanoborohydride (0.25 g) for 12 hours at ambient temperature. Additional aaldehyde or ketone (4 mmol), acetic acid (0.23 mL), and NaBH$_3$CN (0.13 g) is added and the reaction is allowed to continue an additional 24 hours. The mixture is concentrated to dryness, then dissolved in CH$_2$Cl$_2$ and washed sequentially with 5% aq. Na$_2$CO$_3$ and brine, dried over MgSO$_4$, filtered, and evaporated. The product is isolated by silica gel chromatography.

EXAMPLE 28
2'-O-acetyl-4"-O-formyl-erythromycins

Step 1. 2',4"di-O-formylerythromycin. To a stirred solution of the erythromycin (1 mmol) in ether (25 mL) and pyridine (0.5 mL) at 0° C., formic acetic anhydride (18 mmol) is added and the reaction mixture is stirred for 1 hr at 0° C. and 3 hr at 25° C. The reaction mixture is poured onto ice and the Et$_2$O layer is washed with cold saturated NaHCO$_3$ solution, dried with sodium sulfate and concentrated at reduced pressure. The residue is then crystallized from ether or acetonitrile.

Step 2. 4"-O-formylerythromycin. To a solution of the 2',4"-di-O-formylerythromycin (1 mmol) in acetone (10 mL), saturated NaHCO$_3$ solution (10 mL) is added and the reaction mixture is stirred until deemed sufficiently complete by TLC analysis. The volatiles are removed at reduced pressure and the aqueous residue is extracted with methylene chloride. The organic layer is washed with water, dried with sodium sulfate and concentrated at reduced pressure. The residue is then crystallized from ether or acetonitrile.

Step 3. 2-O-acetyl-4"-O-formylerythromycin. To a solution of the 4"-O-formylerythromycin A (1 mmol) in methylene chloride (25 mL) at 0° C., acetic anhydride (1.1 mmol) is added and the reaction mixture is stirred overnight. The excess reagents are quenched by addition of saturated NaHCO$_3$ solution. The organic layer is dried with magnesium sulfate, concentrated under reduced pressure and the residue is recrystallized from acetonitrile.

EXAMPLE 29
11-keto erythromycins

To a solution of 2'-O-acetyl-4"-O-formylerythromycin 6,9-enolether (Example 28, 1 mmol), methylsulfoxide (11 mmol), and dicyclohexylcarbodiimide (3 mmol) in methylene chloride (13 mL) at 0° C., pyridinium trifluoroacetate (3 mmol) is added dropwise. The reaction mixture is stirred 4 hr at room temperature and filtered. The filtrate is washed with water, dried with sodium sulfate and concentrated at reduced pressure. The residue is purified by flash chromatography.

EXAMPLE 30
12-O-alkyl-11-keto erythromycins

To a solution of 2'-O-acetyl-4"-O-formyl 11-deoxy-11-oxoerythromycin 6,9-enolether (Example 29, 1 mmol) in dimethylformamide (15 mL) at 0° C., sodium hydride (1.5 mmol) is added and the reaction mixture is stirred for 20 min. The alkylating agent (e.g., iodomethane to produce 12-O-methyl) (2 mmol) is then added and the reaction mixture is stirred for 2 hr or until deemed complete by TLC. The excess reagents are quenched by addition of saturated NaHCO$_3$ solution and the mixture extracted with ethyl acetate. The combined organic layers are washed with water and brine, then dried with sodium sulfate and concentrated at reduced pressure. The residue is then dissolved in methanol (7.5 mL), saturated NaHCO$_3$ solution (0.5 mL) is added and the reaction mixture is stirred overnight. The reaction mixture is extracted with methylene chloride and the combined organic layers are washed with brine and concentrated at reduced pressure. The residue is purified by flash chromatography.

EXAMPLE 31
11-deoxyerythromycin B 6,9-enolether

A 0° C. solution of 2'-O-acetyl-4"-O-formylerythromycin B 6,9-enolether in THF under an inert atmosphere is treated with 60% sodium hydride and stirred for 30 minutes and allowed to warm to ambient temperature. Carbon disulfide is then added, the reaction mixture is stirred for 1 hour and methyl iodide is added and stirred for an additional hour. The excess reagents are quenched by addition of saturated sodium bicarbonate solution and the volatiles removed under reduced pressure. The aqueous residue is extracted with methylene chloride and the combined organic layers are washed with saturated sodium bicarbonate solution, dried with sodium sulfate, and concentrated under reduced pressure to give the crude product which is dissolved in toluene and heated to reflux under an inert atmosphere. Tributyltin hydride and AIBN are then added and the reaction mixture is kept at reflux temperature for 1 hour and allowed to cool to room temperature. The volatiles are removed at reduced pressure, the residue is dissolved in acetonitrile and then washed repeatedly with hexane. The acetonitrile layer is concentrated under reduced pressure. The residue is purified by flash chromatography and dissolved in methanol, saturated $NaHCO_3$ solution (3% by volume) is added and the reaction mixture is stirred overnight. The reaction mixture is extracted with methylene chloride and the combined organic layers are washed with brine and concentrated at reduced pressure. The residue is purified by flash chromatography.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference.

Citation of the above publications or documents is not intended as an admission that any of the foregoing is pertinent prior art, nor does it constitute any admission as to the contents or date of these publications or documents.

What is claimed is:

1. A method of evaluating the therapeutic efficacy of compounds having agonist activity against a G-protein coupled receptor comprising:

(i) determining a potency value, expressed as a concentration that elicits a response from the G-protein coupled receptor, for a test compound against the G-protein coupled receptor;

(ii) determining a desensitization value, expressed as a concentration that inhibits the original response of the G-protein couple receptor, for the test compound against the G-protein coupled receptor;

(iii) calculating the ratio of the desensitization value over the potency value; and (iv) accepting the test compound for further evaluation if the ratio is more than 10.

2. A method according to claim 1, wherein the G-protein coupled receptor is a motilin receptor.

3. A method according to claim 1, wherein the potency value is expressed as $EC_{50}$ and the desensitization value is expressed as $IC_{50}$.

4. A method according to claim 3, wherein the G-protein coupled receptor is a motilin receptor.

5. The method as claimed in claim 1 wherein, in step (iv), the test compound is accepted for further evaluation if the ratio is more than 100.

6. A method according to claim 5, wherein the G-protein coupled receptor is a motilin receptor.

7. A method according to claim 5, wherein the potency value is expressed as $EC_{50}$ and the desensitization value is expressed as $IC_{50}$.

8. A method according to claim 7, wherein the G-protein coupled receptor is a motilin receptor.

* * * * *